United States Patent
De Wael et al.

(10) Patent No.: US 12,313,583 B2
(45) Date of Patent: May 27, 2025

(54) ELECTROCHEMICAL MEASUREMENT OF PRIMARY OR SECONDARY AMINES

(71) Applicant: UNIVERSITEIT ANTWERPEN, Antwerp (BE)

(72) Inventors: Karolien De Wael, Sint-Pauwels (BE); Saranya Thiruvottriyur Shanmugam, Chennai (IN)

(73) Assignee: UNIVERSITEIT ANTWERPEN, Antwerp (BE)

( * ) Notice: Subject to any disclaimer, the term of this patent is extended or adjusted under 35 U.S.C. 154(b) by 514 days.

(21) Appl. No.: 17/638,370

(22) PCT Filed: Aug. 31, 2020

(86) PCT No.: PCT/EP2020/074252
§ 371 (c)(1),
(2) Date: Feb. 25, 2022

(87) PCT Pub. No.: WO2021/038111
PCT Pub. Date: Mar. 4, 2021

(65) Prior Publication Data
US 2022/0326172 A1    Oct. 13, 2022

(30) Foreign Application Priority Data

Aug. 30, 2019 (EP) .................... 19194726

(51) Int. Cl.
*G01N 27/30* (2006.01)
*G01N 27/48* (2006.01)
*G01N 27/49* (2006.01)

(52) U.S. Cl.
CPC .......... *G01N 27/307* (2013.01); *G01N 27/48* (2013.01); *G01N 27/49* (2013.01)

(58) Field of Classification Search
None
See application file for complete search history.

(56) References Cited

FOREIGN PATENT DOCUMENTS

| EP | 0343791 B1 | 7/1992 |
|---|---|---|
| GB | 462319 A | 3/1937 |
| JP | S59142462 A | 8/1984 |

OTHER PUBLICATIONS

B. B. Thompson, "The Mannich Reaction", Journal of Pharmaceutical Sciences, 57(5): p. 715-733, May 1968.*
International Search Report with Written Opinion from PCT Application No. PCT/EP2020/074252, Dec. 10, 2020.
Extended Search Report from corresponding EP Application No. 19194726.6, Feb. 20, 2020.
Suslu et al., "Indirect Square-Wave Voltammetric Determination of Cefepime in the Presence of Formaldehyde," Latin American Journal of Pharmacy, vol. 35, No. 10, Aug. 7, 2016, pp. 2246-2253.
Ren et al., "Piezoelectric Sensor Sensitive to Nitrobenzene Based on a Cyclohexanone-Formaldehyde Coating," Analytica Chimica Acta, Elsevier Science, vol. 286, No. 2, Feb. 18, 1994, pp. 197-203.
Sun et al., "Adsorptive Stripping Voltammetric Determination of Netilmicin in the Presence of Formaldehyde," Analytical and Bioanalytical Chemistry, Springer, vol. 385, No. 1, Apr. 8, 2006, pp. 161-167.
Douglas et al., "Investigation of Molybdenum-(Resorcinol-formaldehyde) (Mo-RF) Electrode for Alkaline Electrolyser Operation," International Journal of Hydrogen Energy, vol. 36, Issue 13, Jan. 19, 2011, pp. 7791-7798.
Goodwin et al., "Tagging of Model Amphetamines with Sodium 1,2-Naphthoquinone-4-sulfonate: Application to the Indirect Electrochemical Detection of Amphetamines in Oral (Saliva) Fluid," Electroanalysis, Jul. 6, 2006, vol. 18, Issue 18, pp. 1833-1837.
Ivison et al., "Development of a Redox Mediated Amperometric Detection System for Immunoassay. Application to Urinary Amphetamine Screening," Electroanalysis, vol. 12, Issue 10, Jan. 4, 2000, pp. 778-785.
European Office Action from corresponding EP Application No. 20768286.5, Jun. 11, 2024.

* cited by examiner

*Primary Examiner* — J. Christopher Ball
(74) *Attorney, Agent, or Firm* — Workman Nydegger

(57) ABSTRACT

A source of formaldehyde for methylating a primary or secondary amine is part of an electrochemical measurement. The source of formaldehyde may be an adduct of formaldehyde.

13 Claims, 11 Drawing Sheets

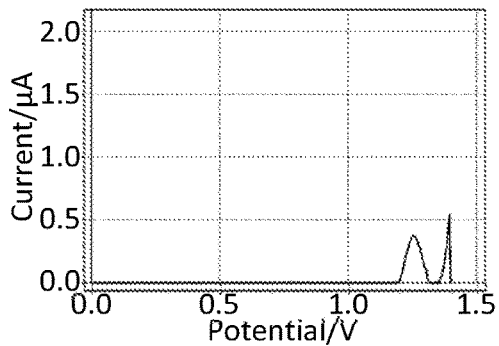
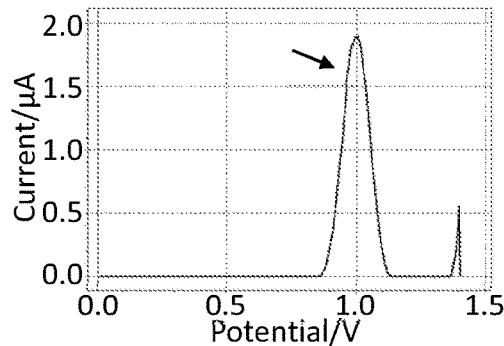
FIG 5a
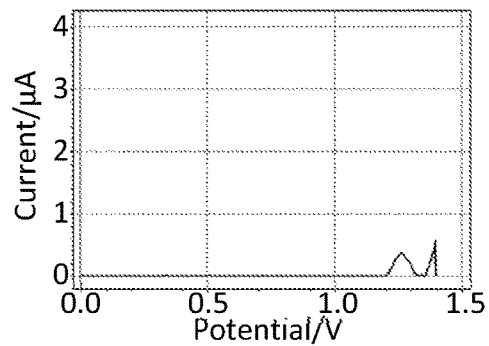
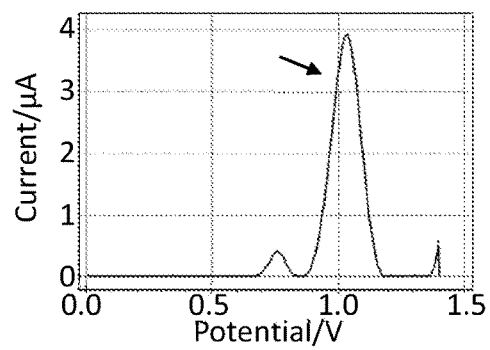
FIG 5b
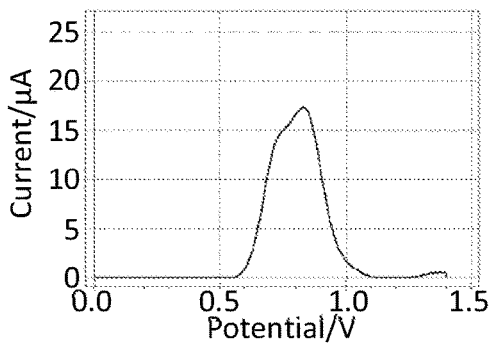
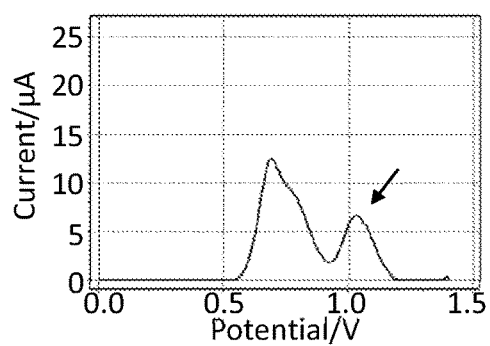
FIG 5c
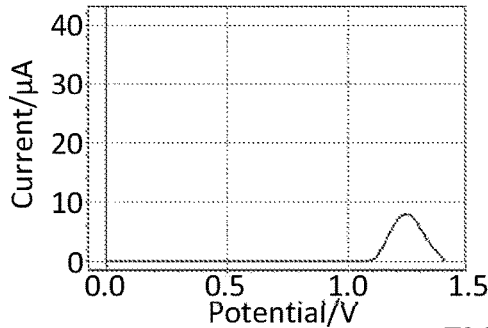
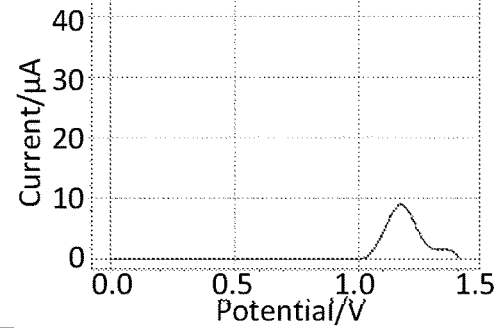
FIG 5d
FIG 5

FIG 5e 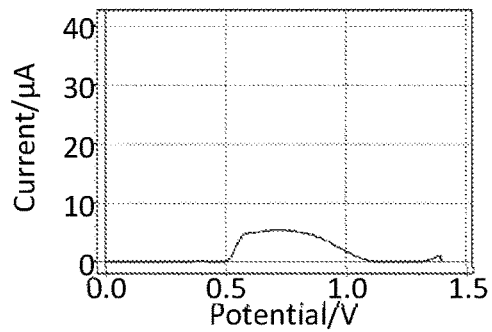 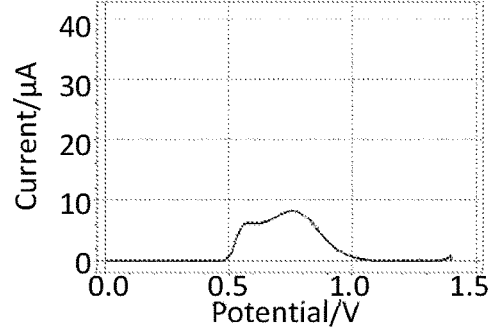
FIG 5f 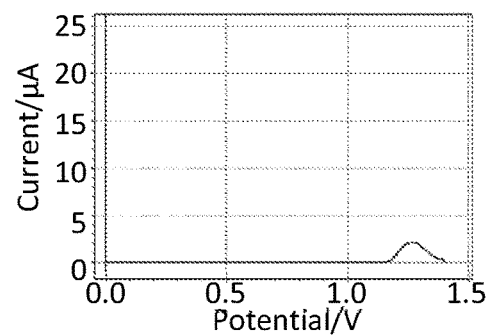 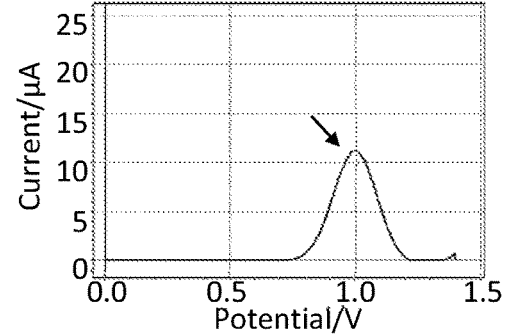
FIG 5g 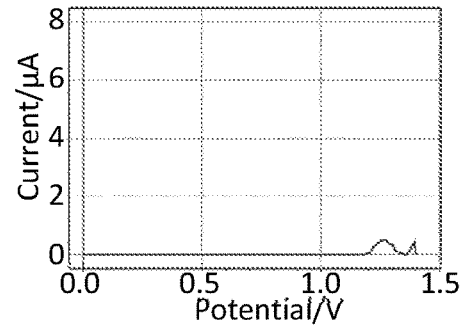 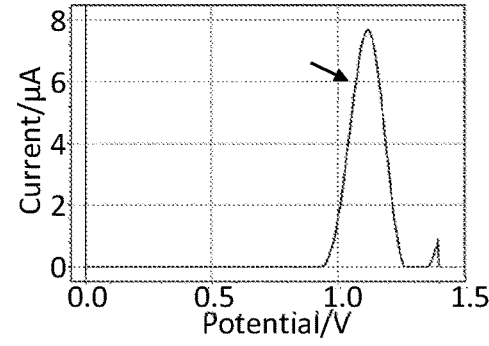
FIG 5h 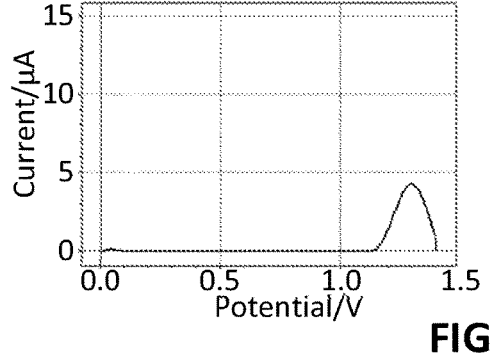 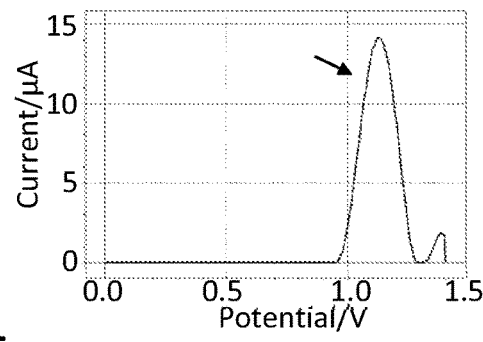
FIG 5

FIG 7a
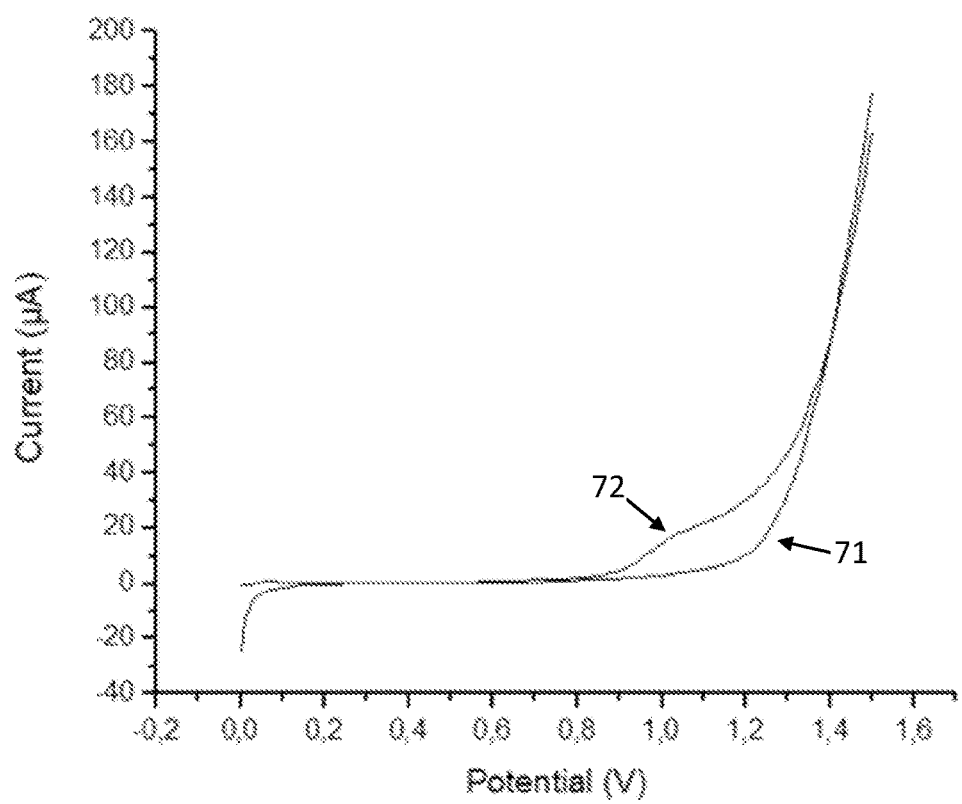
FIG 7b
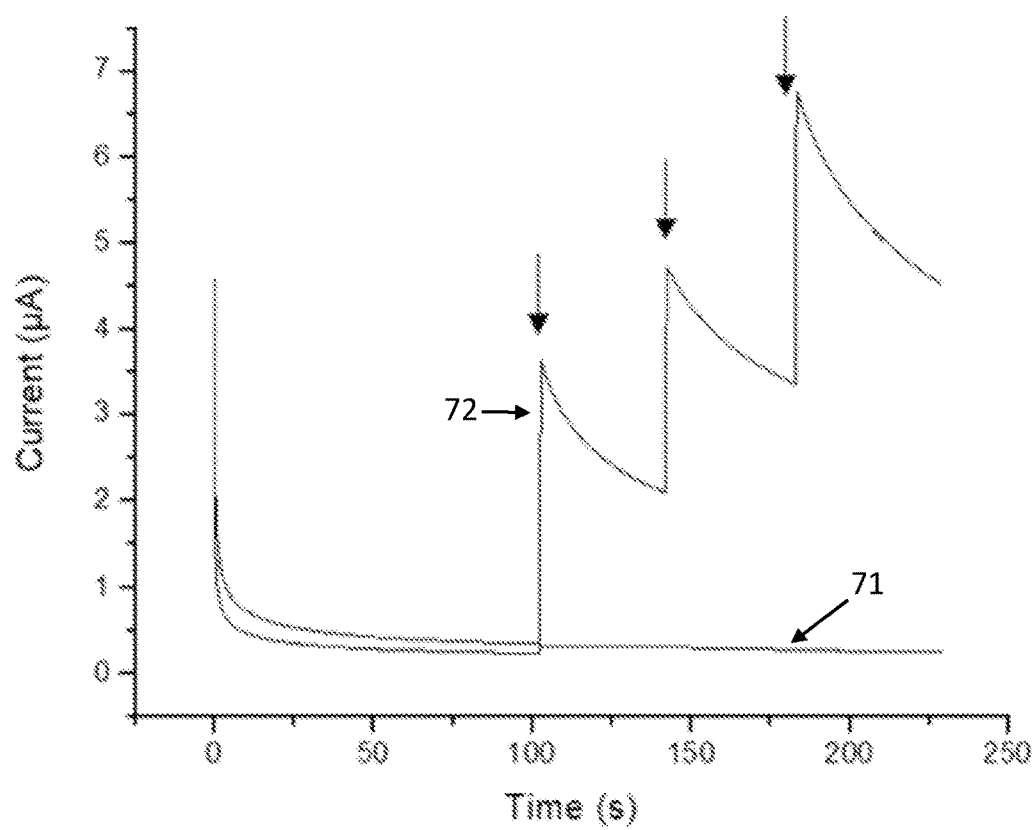
FIG 7

ELECTROCHEMICAL MEASUREMENT OF PRIMARY OR SECONDARY AMINES

TECHNICAL FIELD OF THE INVENTION

The present invention relates to the electrochemical measurement (e.g. detection) of amines and more particularly to strategies for the measurement of primary or secondary amines.

BACKGROUND OF THE INVENTION

The electrochemical oxidation of aliphatic and aromatic amines has been widely investigated. When oxidized, they form radical cations in the vicinity of the electrode material. For secondary and tertiary amines, these cation radicals vary from stable to short-lived, but they are electrochemically detectable within the potential window of the commonly used electrode systems; even in aqueous buffers. The oxidation potentials of secondary amines are higher than those of tertiary amines in similar measuring conditions. Conversely, the radical cations of primary amines are very short-lived and their oxidation potentials are higher than for secondary and tertiary amines. These oxidation potentials are typically out of the working potential windows of the commonly used electrode systems. The ease of electrochemical detection (and measurement in general) thus follows a general trend of tertiary>secondary>primary amines.

One particular example of a primary amine is amphetamine, which is a synthetic stimulant drug belonging to the group of amphetamine-type stimulants (ATS). Due to its addictive and other adverse properties, amphetamine is a controlled substance and it is therefore of utmost importance to possess rapid, selective, and sensitive methods to identify amphetamine in illegal street samples and wastes. Chromatographic methods coupled with mass spectrometric detection, such as liquid chromatography-mass spectrometry (LC-MS), gas chromatography-mass spectrometry (GC-MS) or gas chromatography-flame ionization detector (GC-FID) are the common laboratory methods used to detect amphetamine. These are however expensive and labour-intensive techniques and often include sample preparation steps (e.g. derivatization) before analysis. FT-IR spectroscopy and Raman spectroscopy offer higher portability but require expensive instruments and experience difficulties with coloured samples due to fluorescence. Meanwhile, immunoassays mainly focus on the detection of drug metabolites in body fluids.

Electrochemical detection could address these concerns and offer a reliable and practical solution in the field. However, while there is plenty of research on electrochemical detection of other ATS and other classes of drugs, as a primary amine (and thus difficult to detect electrochemically, cf. supra), limited literature can be found for electrochemical detection of amphetamine. Indirect electrochemical detection by labelling of amphetamine with sodium 1,2-naphthoquinone-4-sulfonate was carried out by Goodwin et. al. (GOODWIN, Alexander; BANKS, Craig E.; COMPTON, Richard G. Tagging of Model Amphetamines with Sodium 1, 2-Naphthoquinone-4-sulfonate: Application to the Indirect Electrochemical Detection of Amphetamines in Oral (Saliva) Fluid. *Electroanalysis: An International Journal Devoted to Fundamental and Practical Aspects of Electroanalysis*, 2006, 18.18: 1833-1837.).

An immunoassay for amphetamine in urine specimens, with electrochemical detection, was developed by Ivison et al. using enzyme multiplied immunoassay technique reagents and involves complex enzymatic assays steps (IVISON, Fiona M., et al. Development of a redox mediated amperometric detection system for immunoassay. application to urinary amphetamine screening. *Electroanalysis: An International Journal Devoted to Fundamental and Practical Aspects of Electroanalysis*, 2000, 12.10: 778-785.)

There is thus still a need in the art for better methods for electrochemically detecting primary and—to a lesser extent also—secondary amines

SUMMARY OF THE INVENTION

It is an object of the present invention to provide good methods for electrochemically detecting primary or secondary amines. It is a further object of the present invention to provide products associated therewith. This objective is accomplished by uses, methods, electrochemical electrodes and kits-of-parts according to the present invention.

It is an advantage of embodiments of the present invention that the oxidation potential of the primary or secondary amines can be brought into a more electrochemically accessible potential window and/or can yield an enriched signal fingerprint.

It is an advantage of embodiments of the present invention that primary and secondary amines can be detected in a rapid, selective and/or sensitive manner. It is a further advantage of embodiments of the present invention that they are well-suited for use in the field.

It is an advantage of embodiments of the present invention that primary or secondary amines can be detected in the presence of various interferents.

It is an advantage of embodiments of the present invention that they apply broadly to all primary or secondary amines, including drugs of abuse, amino acids and antibiotics.

It is an advantage of embodiments of the present invention that they can operate well as such and do not require the use of a catalyst.

It is an advantage of embodiments of the present invention that an electrochemical electrode can be made which is pre-coated and ready for use. It is a further advantage of embodiments of the present invention that the electrochemical electrodes can be easy to use, compatible with commonly available measuring systems, relatively cheap and disposable.

It is an advantage of embodiments of the present invention that they can be realized in a relatively straightforward and economical fashion.

It is an advantage of embodiments of the present invention that widely available commercial products can be used.

In a first aspect, the present invention relates to a use of a source of formaldehyde for methylating a primary or secondary amine as part of an electrochemical measurement. The source of formaldehyde may in particular be an adduct of formaldehyde.

In a second aspect, the present invention relates to a method for electrochemically detecting a primary or secondary amine, comprising: (a) providing a sample which potentially comprises the primary or secondary amine; (b) contacting the sample with a source of formaldehyde, thereby, if present, methylating the primary or secondary amine to yield a methylated amine; (c) performing an electrochemical technique on the sample to obtain measurement results concerning the methylated amine, and (d) analysing the measurement results.

In a third aspect, the present invention relates to an electrochemical electrode for use in a method according to any embodiment of the second aspect, comprising a coating of a source of formaldehyde.

In a fourth aspect, the present invention relates to a kit-of-parts for use in a method according to any embodiment of the second aspect, comprising: (i) an electrochemical electrode, and (ii) a source of formaldehyde.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIGS. 1a and 1b, shows square-wave voltammograms (1a) and baseline corrected square-wave voltammograms (1b) showing the effect of formaldehyde in measuring amphetamine. Solid line: 1 mM amphetamine in a pH 7 phosphate buffer solution (PBS) solution containing 11.1% formaldehyde. Dotted line: 1 mM amphetamine in a pH 7 PBS without formaldehyde. Dashed line: blank pH7 PBS containing 11.1% formaldehyde.

FIGS. 2a to 2d, shows extracted ion chromatograms of reaction samples, in PBS with 11.1% formaldehyde, of amphetamine at pH 7 (2a), methamphetamine at pH 7 (2b), amphetamine at pH 12 (2c) and methamphetamine at pH 12 (2d).

FIG. 5, including FIGS. 5a to 5h, shows square-wave voltammograms of 1 mM primary amine fluoroamphetamine (5a), 2-aminoindane (5b), dimethocaine (5c), cephalexin (5d), amoxycycline (5e), phenyl glycine (5f), glycine (5g) and histidine (5h) in pH 7 phosphate buffer solution (i.e. without formaldehyde; left) and pH7 formate-formaldehyde buffer solution with 3.7% formaldehyde (right).

FIG. 7, including FIGS. 7a and 7b, shows linear sweep voltammograms at 100 mV/s (7a) and chronoamperograms at 1.0 V (7b) for 1 mM amphetamine in phosphate buffer solution (71) and formaldehyde-formate buffer solution (72).

Figure 1:
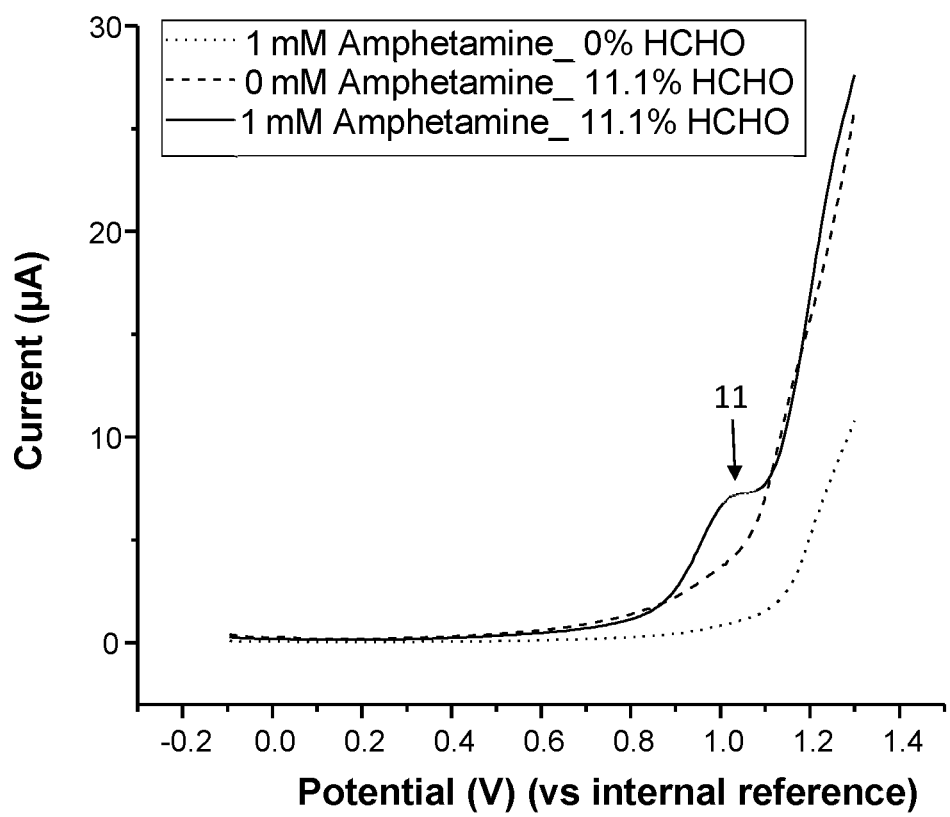
FIG. 1, including
Figure 1:
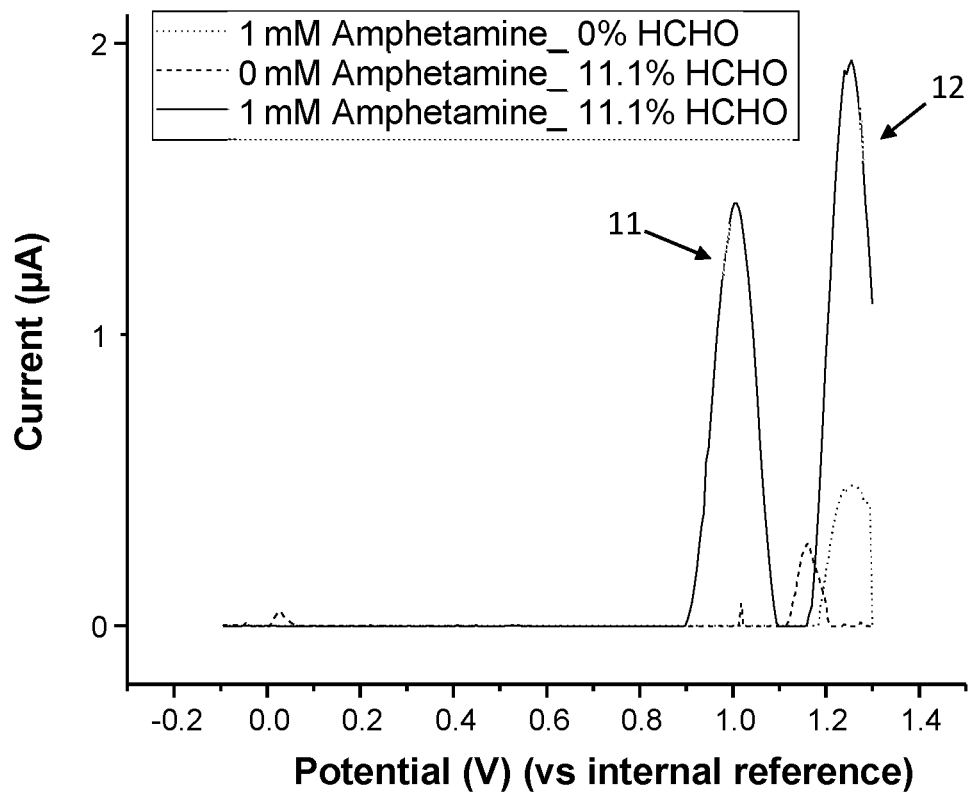

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms over, under and the like in the description and the claims are used for descriptive purposes and not necessarily for describing relative positions. It is to be understood that the terms so used are interchangeable with their antonyms under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. The term "comprising" therefore covers the situation where only the stated features are present and the situation where these features and one or more other features are present. Thus, the scope of the expression "a device comprising means A and B" should not be interpreted as being limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In a first aspect, the present invention relates to a use of a source of formaldehyde for methylating a primary or secondary amine as part of an electrochemical measurement.

It was surprisingly found within the present invention that adding a source of formaldehyde to an electrochemical measurement environment improves the electrochemical measurement (e.g. detection) of primary and secondary amines. Without being bound by theory, it is believed that the source of formaldehyde acts as a direct or indirect methylation agent for the primary or secondary amine, e.g. through a kind of in-situ Eschweiler-Clarke reaction. The reaction scheme of such an Eschweiler-Clarke methylation for a primary amine, using formaldehyde as a direct methylation agent and formate as a source of hydride, is as follows:

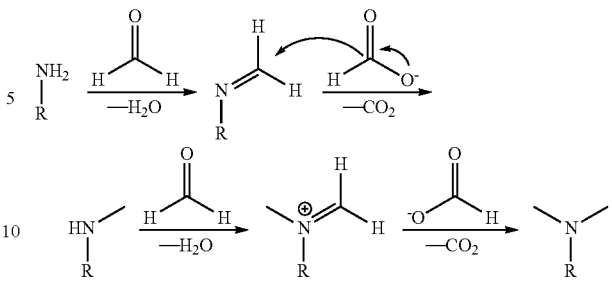

The reaction is thus normally initiated when formaldehyde and the primary amine form an imine intermediate in the first step. Formic acid (or formate) acts as a soft reducing agent and reduces the imine to a secondary amine by transferring a hydride. However, the reaction does not necessarily stop there, and a tertiary amine can also be formed by the same reaction mechanism. For example, the Eschweiler-Clarke reaction scheme for methylation and dimethylation of amphetamine is as follows:

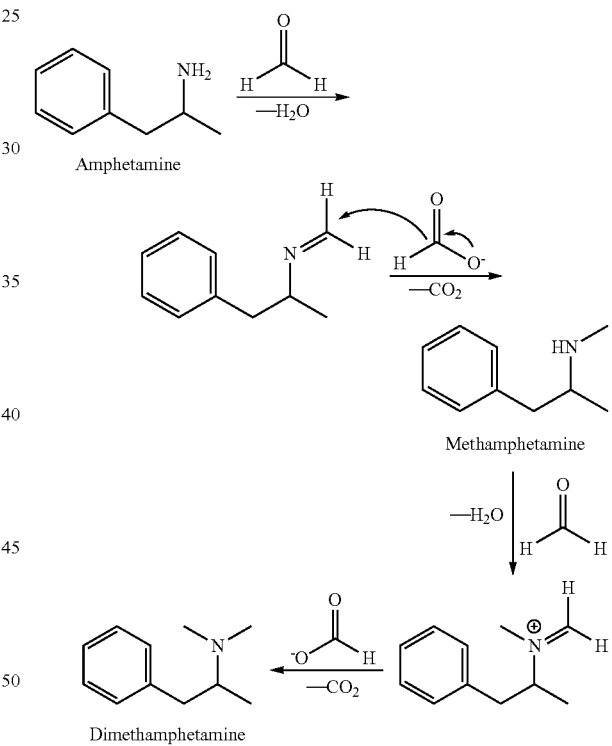

As such, it is believed that the source of formaldehyde methylates (i.e. acts as a direct or indirect methylation agent) the primary or secondary amine. For primary amines, methylation to form a secondary amine typically brings the oxidation of the methylated amine within the working potential window of the commonly used electrode systems and thus makes it electrochemically detectable. For secondary amines (or dimethylation of primary amines), the methylation reaction to form a tertiary amine is typically incomplete, thus yielding a mixture of secondary and tertiary amines. In that case, methylation then typically leads to an enriched fingerprint as compared to the original amine (i.e. in absence of methylation).

It will be clear that "methylating a primary or secondary amine as part of an electrochemical measurement" refers to a methylation being performed shortly prior to or concurrent with the electrochemical measurement, where the electrochemical measurement aims to measure some aspect related to the primary or secondary amine (e.g. detect its presence) and the methylation facilitates achieving that aim (e.g. by bringing the oxidation potential in a more accessible potential window or yielding an enriched signal fingerprint). As such, methylating a primary or secondary amine with a source of formaldehyde as a general synthesis step (be it a final or intermediate step), with the aim of forming some desired synthesis product, and then afterwards performing an electrochemical measurement on said synthesized product as a kind of characterization step, is herein not considered to be "methylating [ . . . ] as part of an electrochemical measurement". In embodiments, the source of formaldehyde may be present in an electrochemical measurement environment in which the electrochemical measurement is performed. In embodiments, the electrochemical measurement environment may comprise a measurement solution (e.g. a measurement buffer; cf. infra). In embodiments, formaldehyde may be present in the electrochemical measurement environment. In embodiments, a duration between the start of the methylation and the start of the electrochemical measurement may be from 0 s (i.e. immediately) to 60 min, preferably from 15 s to 20 min, yet more preferably from 30 s to 10 min, most preferably from 45 s to 2 min, such as 1 min.

In embodiments, the use of the source of formaldehyde may be for electrochemically detecting the primary or secondary amine.

Although the source of formaldehyde may be formaldehyde (e.g. formalin); it is within the present invention more preferably an adduct of formaldehyde. Adducts of formaldehyde are typically less prone to oxidation and other stability issues than formaldehyde as such, products based on such adducts are therefore characterized by a longer shelf-life. Moreover, they are more reliable and practical in the field—where environmental parameter (e.g. temperature) are not easily controlled as in lab-setting—, making them more suited therefor. Because concentrated formaldehyde is fairly unstable, it is typically stored, commercialized and/or used as an aqueous solution (e.g. 37 wt %) that is also referred to as 'formalin'. A small amount of stabilizer (e.g. 10-12% methanol) is usually added to such an aqueous formaldehyde solution so as to further suppress oxidation and polymerization of the formaldehyde. Nevertheless, a typical aqueous formaldehyde solution can comprise a significant amount of formaldehyde in the form of oligomers of various lengths—as opposed to monomeric formaldehyde. In this light, an adduct of formaldehyde may— in embodiments—be such that an aqueous solution thereof has a lower ratio of monomeric formaldehyde to oligo- and/or polymeric formaldehyde than a typical commercial-grade aqueous formaldehyde solution (e.g. than a typical commercial-grade 37 wt % aqueous formaldehyde solution); preferably at least 2 times lower, more preferably at least 5 times lower, yet more preferably at least 10 times lower, most preferably at least 20 times lower.

In preferred embodiments, the adduct of formaldehyde may intrinsically (i.e. when considered as such, e.g. when it is not dissolved in a solvent) be a solid compound (e.g. a powder) at room temperature (e.g. at 20° C.). In contrast to formaldehyde as such, which is intrinsically a gas at room temperature (though it is most typically in the form of a solution; cf. supra), paraformaldehyde, 1,3,5-trioxane and similar adducts of formaldehyde are typically intrinsically solid at room temperature. This difference in phase further contributes the stability and practicality mentioned above, as compounds in the solid phase are typically less reactive than in the liquid or gas phase and convenient products can be formulated—for instance as (solid) coatings on an electrochemical electrode (cf. infra).

In embodiments, the adduct of formaldehyde may be an oligomer (e.g. dimer, trimer, etc.) or a polymer (e.g. paraformaldehyde) comprising formaldehyde. In embodiments, the oligomer or polymer may be a linear or cyclic. In embodiments, the oligomer or polymer may be a homooligo- or polymer (i.e. consisting of formaldehyde) or a heterooligo- or polymer (i.e. comprising formaldehyde alongside at least one other monomer). In preferred embodiments, the adduct of formaldehyde may be paraformaldehyde or 1,3,5-trioxane. Paraformaldehyde and 1,3,5-trioxane are advantageously adducts of formaldehyde which are readily commercially available. Like other adducts of formaldehyde, they are both advantageously typically more stable than formaldehyde as such, thus allowing e.g. a longer shelf-life for products (e.g. cf. embodiments of the third or fourth aspect) based on them.

Note that formaldehyde is in the presence of water (e.g. in aqueous solution) in equilibrium with its hydrate, methanediol. As such, as is common in the art, adducts of methanediol are also considered to be adducts of formaldehyde. Indeed, for example paraformaldehyde is typically considered a polymer of formaldehyde, but could likewise be considered as an adduct of methanediol.

As seen in the above reaction schemes, at least in the Eschweiler-Clarke reaction, the direct methylation agent is typically formaldehyde. As such, in order to methylate the primary or secondary amine, the source of formaldehyde is typically such that it yields formaldehyde in the electrochemical measurement environment. Adducts of formaldehyde will thus typically act as indirect methylation agents, first yielding formaldehyde which then operates as the direct methylation agent. Nevertheless, it is not excluded that an adduct of formaldehyde may in certain instances anyway perform as a direct methylation agent.

In embodiments, the primary or secondary amine may be essentially any primary or secondary amine. In particular embodiments, the primary or secondary amine may be selected from the list of drugs of abuse, amino acids and antibiotics.

In embodiments, any feature of any embodiment of the first aspect may independently be as correspondingly described for any embodiment of any of the other aspects.

In a second aspect, the present invention relates to a method for electrochemically detecting a primary or secondary amine, comprising: (a) providing a sample which potentially comprises the primary or secondary amine; (b) contacting the sample with a source of formaldehyde, thereby, if present, methylating the primary or secondary amine to yield a methylated amine; (c) performing an electrochemical technique on the sample to obtain measurement results concerning the methylated amine, and (d) analysing the measurement results.

In embodiments, the method for electrochemically detecting the primary amine may be for detecting the primary amine (or rather the methylated amine) in a more accessible potential window (cf. supra). In embodiments, the method for electrochemically detecting the secondary amine may be for detecting an enriched signal thereof (cf. supra). In embodiments, if the method is for detecting a primary amine, the methylated amine may be a secondary or tertiary amine. In embodiments, if the method is for detecting a secondary amine, the methylated amine may be a tertiary amine.

In embodiments, step b may comprise: (b1) bringing the sample in contact with an electrochemical electrode comprising a coating of the source of formaldehyde, and/or (b2) forming a mixture of the sample and the source of formaldehyde.

In embodiments, the electrochemical electrode in step b1 may according to an embodiment of the third aspect.

In embodiments, step b2 may be performed before or after bringing the source of formaldehyde in contact with an electrochemical electrode. For example, the electrochemical electrode could be contacted with a solution (e.g. a buffer solution; cf. infra) comprising the source of formaldehyde and the sample could then be mixed into said solution, or the sample and the source of formaldehyde could be mixed before bringing the mixture in contact with the electrochemical electrode.

In preferred embodiments, the sample may be an aqueous solution. In embodiments, the aqueous solution may be a buffer solution. In embodiments, the buffer solution may be a phosphate buffer solution (PBS) or a formaldehyde formate buffer solution (FFBS). In embodiments, the phosphate buffer may comprise $KH_2PO_4$. In embodiments, the phosphate buffer solution may comprise potassium chloride (KCl) and potassium phosphate ($KH_2PO_4$); such as comprising (e.g. consisting of) 0.1 M potassium chloride and 0.02 M potassium phosphate. It was observed that the latter phosphate buffer solution advantageously resulted in enough ionic strength to yield a sharper signal, as compared to e.g. a phosphate buffer solution without KCl In embodiments, the formaldehyde formate buffer solution may comprise potassium chloride, potassium phosphate, formaldehyde ($CH_2O$) and sodium formate (HCOONa), such as comprising (e.g. consisting of) 0.1 M potassium chloride, 0.1 M potassium phosphate, 10 vol % of 37% formaldehyde and 20 vol % of 10 M sodium formate. In other embodiments, the sample may be an organic solvent, such as ethanol. While methylation is possible in certain organic solvents, it typically requires an experimental setup which is less common (e.g. requiring special solvent-resistant electrodes) and may therefore be less preferred. In yet other embodiments, the sample may be a solid sample. Such a solid sample could for example be mixed into a solution comprising the source of formaldehyde (cf. supra).

In embodiments, the electrochemical electrode may be a screen-printed electrode (SPE), such as a carbon screen-printed electrode (which can alternatively be referred to as 'graphite screen-printed electrodes').

In embodiments, bringing the sample in contact with the electrochemical electrode may comprise dropping an amount (e.g. from 1 µl to 10 ml, preferably from 20 µl to 1 ml, yet more preferably from 50 µl to 200 such as 800) of the sample onto the electrochemical electrode.

In embodiments, the sample may have an analyte concentration (e.g. concentration of the primary or secondary amine) of from 0.1 to 100 mM, preferably from 0.5 to 10 mM, such as 1 mM.

In embodiments, step b may be performed under conditions of neutral (e.g. pH 7) or basic pH (e.g. a pH above 7 up to 14, preferably from 8 to 13, more preferably from 10 to 12, such as 12). In embodiments, the source of formaldehyde may be an adduct of formaldehyde and step b may be performed under conditions of basic pH. A basic pH advantageously promotes the depolymerization of the adduct into formaldehyde. Moreover, if the source of formaldehyde is present in a hydrogel matrix, a basic pH advantageously promotes swelling of the source of formaldehyde and release of the source of formaldehyde into the measuring environment.

In embodiments, step b may be performed in presence of a source of hydride. In embodiments, the source of hydride may be formic acid (or formate). The formic acid may for example have been formed from the formaldehyde, e.g. by oxidation from atmospheric oxygen. Formation of formic acid/formate from formaldehyde is especially present in basic conditions (e.g. pH 12), but also occurs under neutral conditions. In particular, it was observed that, although the presence of a source of hydride is required according to the Eschweiler-Clarke reaction mechanism, methylation still occurs if no specific source of hydride (other than the source of formaldehyde) is added to the electrochemical measurement environment.

In embodiments, a duration between the start of step b and the start of step c may be from 0 s (i.e. immediately) to 60 min, preferably from 15 s to 20 min, yet more preferably from 30 s to 10 min, most preferably from 45 s to 2 min, such as 1 min.

In embodiments, the electrochemical technique may comprise a voltammetry or amperometry. In embodiments, the voltammetry may be square-wave voltammetry or a linear sweep voltammetry. In embodiments, the amperometry may be a chronoamperometry.

In embodiments, the measurements results obtained in step c may concern the methylated amine in that they reflect whether or not the methylated amine is present. In other embodiments, the measurement results obtained in step c may concern the methylated amine in that they reflect a measurement quantity of the methylated amine is present.

In embodiments, step d may comprise determining a measurement quantity of the methylated amine. In embodiments, the measurement quantity may be selected from an oxidation potential, a fingerprint or a concentration. In embodiments, the measurement quantity may be found within a potential window of from 0.5 to 1.5 V, preferably from 0.6 to 1.2 V, yet more preferably from 0.8 to 1.0 V. In embodiments, the method may a method for electrochemically measuring a primary or secondary amine, comprising: (a) providing a sample which comprises the primary or secondary amine; (b) contacting the sample with a source of formaldehyde, thereby methylating the primary or secondary amine to yield a methylated amine; (c) performing an electrochemical technique on the sample to obtain measurement results concerning the methylated amine, and (d) analysing the measurement results.

In embodiments, the source of formaldehyde may be present in a matrix. In embodiments, the matrix may be a hydrogel. In preferred embodiments, the hydrogel may be gelatine. In other embodiments, the hydrogel may be a non-ionic hydrogel. Providing the source of formaldehyde in a matrix advantageously contributes to the stability of the source of formaldehyde, thereby e.g. improving its long-term stability and thereby its ability to be commercialized (cf. infra). For example, the shelf-life could be extended to several weeks or even several months. Gelatine is a polyampholyte hydrogel which has proven to perform particularly well when used as a matrix for the source of formaldehyde.

In embodiments, any feature of any embodiment of the second aspect may independently be as correspondingly described for any embodiment of any of the other aspects.

In a third aspect, the present invention relates to an electrochemical electrode for use in a method according to any embodiment of the second aspect, comprising a coating of a source of formaldehyde.

In embodiments, the electrochemical electrode may comprise a working electrode and/or a counter electrode and/or a reference electrode. In embodiments, the electrochemical electrode may be a singular (i.e. an electrode with a single electrode functionality—e.g. working, counter or reference—at any given time) or combination electrode (i.e. an electrode which combines two or more electrode functionalities in a single body). To facilitate distinction between a combination electrode and the electrodes comprised therein, an electrochemical electrode which can comprise multiple electrodes could alternatively be referred as an 'electrochemical electrode body'. In embodiments, the electrochemical electrode may be a screen-printed electrode (SPE), such as a carbon screen-printed electrode (which can alternatively be referred to as 'graphite screen-printed electrodes').

In embodiments, the electrochemical electrode may comprise a working electrode, and a counter electrode and/or a reference electrode, and the coating of the source of formaldehyde may cover the working electrode. In embodiments, the coating of the source of formaldehyde may not cover the counter and/or the reference electrode. The coating preferably covers the working electrode, such that the source of formaldehyde is in close vicinity to where the amine will be measured; but not the counter and/or reference electrode, so that their operation is not complicated or disturbed.

In embodiments, forming the electrochemical electrode may comprise: forming a mixture—such as a dispersion (e.g. a solution, colloid or suspension) of the source of formaldehyde, contacting the mixture to the electrochemical electrode and drying the electrochemical electrode. In embodiments, forming the mixture may be performed such that a mixture of from 5 to 50 mg/ml, preferably from 10 to 35 mg/ml, such as 20 mg/ml of the source of formaldehyde (e.g. paraformaldehyde) is obtained. In embodiments, forming the mixture may comprise mixing the source of formaldehyde in a polar solvent (e.g. ethanol, such as 70% ethanol). In embodiments, contacting the mixture to the electrochemical electrode may comprise dropping (e.g. drop casting) the mixture (e.g. from 1 to 100 µl thereof, preferably from 2 to 500, yet more preferably from 3 to 10 µl, such as 5 µl) onto the electrochemical electrode. In embodiments, drying the electrochemical electrode may comprise air-drying the electrochemical electrode (for instance until the solvent has been completely evaporated, e.g. 45 min).

In embodiments, the coating may comprise a matrix and the source of formaldehyde. In embodiments, the matrix may be a hydrogel. In preferred embodiments, the hydrogel may be gelatine. In other embodiments, the hydrogel may be a non-ionic hydrogel. Gelatine is a polyampholyte hydrogel which has proven to perform particularly well when used as a matrix in the present electrochemical electrode.

In such embodiments, forming the electrochemical electrode may comprise: (a) mixing the matrix in a solution, (b) mixing the source of formaldehyde into the mixture of step a, (c) contacting the mixture of step b to the electrochemical electrode, and (d) drying the electrochemical electrode. In embodiments, step a may comprise mixing (e.g. until a homogeneous mixture is obtained) the matrix (e.g. 1.5 wt % gelatine, such as 1.5 wt % gelatine B) in a buffer solution (e.g. pH 7 PBS). In embodiments, step a may further comprise heating the mixture of the matrix in the solution to a temperature of from 30 to 60° C., preferably 40° C. for a period of from 5 to 30 min, preferably 15 min. In embodiments, step b may be performed such that a mixture of from 5 to 50 mg/ml, preferably from 10 to 35 mg/ml, such as 20 mg/ml of the source of formaldehyde (e.g. paraformaldehyde) in the mixture of step a is obtained. In embodiments, step c may comprise dropping the mixture of step b (e.g. from 1 to 100 µl thereof, preferably from 2 to 50 µl, yet more preferably from 3 to 10 µl, such as 5 µl) onto the electrochemical electrode. In embodiments, step d may comprise air-drying the electrochemical electrode (until the solvent has been completely evaporated, e.g. 45 min).

In other embodiments, —rather than coating the matrix with the source of formaldehyde onto the electrochemical electrode (cf. step b 1 of the second aspect)—this matrix with the source of formaldehyde as such may be mixed with the sample (cf. step b2 of the second aspect). To that effect, the mixture of step b may be used as such, or it may be processed into a dried product (e.g. powder or granules) that may be more easily handled (e.g. due to improved/facilitated storage, transportation, dosage, etc.) and can then be mixed with the sample.

Between different types of coated electrochemical electrodes and products that can be mixed with the sample, several different commercially interesting products can thus be made based on sources of formaldehyde.

In embodiments, any feature of any embodiment of the third aspect may independently be as correspondingly described for any embodiment of any of the other aspects.

In a fourth aspect, the present invention relates to a kit-of-parts for use in a method according to any embodiment of the second aspect, comprising: (i) an electrochemical electrode, and (ii) a source of formaldehyde.

In embodiments, the kit-of-parts may be combined with a potentiostat to form an electrochemical measurement system.

In embodiments, any feature of any embodiment of the fourth aspect may independently be as correspondingly described for any embodiment of any of the other aspects.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

Example 1: Electrochemical Detection of Amphetamine

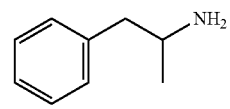

To illustrate the present invention, different measurements were performed on amphetamine (see chemical structure above) as a model primary amine analyte in order to validate the use of formaldehyde in the measurement environment as a methylating agent for the analyte and thereby enable its electrochemical detection (e.g. through detection of methylated and di-methylated forms of said primary amine analyte). To this end, different strategies (cf. examples 1a-c below) were developed which enable to make the formaldehyde available in the measuring environment.

EXPERIMENTAL

Drugs of abuse standards were purchased from Lipomed (Arlesheim, Switzerland). Other standards were purchased from Sigma Aldrich (Darmstadt, Germany). Real street samples were obtained from the National Institute for Criminalistics and Criminology (Brussels, Belgium). Gelatine gel B was supplied by PB gelatins (Pontypridd, United Kingdom). Carbon ItalSens IS-C Screen-Printed Electrodes (SPE) were purchased from PalmSens (Utrecht, The Netherlands) and were used during all electrochemical measurements. Electrochemical measurements were performed using a Metrohm (Antwerp, Belgium) Autolab 302 potentiostat and NOVA 1.11 software or using a Palmsens Multistat potentiostat and Multitrace software.

Example 1a: Addition of Formaldehyde in the Measuring Buffer Solution (Strategy 1)

Square-Wave Voltammetry of Amphetamine in the Presence of Formaldehyde

As an initial proof of concept, a 1 mM solution of amphetamine sulphate in phosphate buffer solution containing 0.1 M KCl and 0.02 M $KH_2PO_4$ (PBS) with and without 11.1% formaldehyde was subjected to a square-wave voltammetry (SWV) measurement. FIG. 1a shows the resulting voltammograms, clearly indicating an oxidative peak (11) at ca. 1.03 V for 1 mM amphetamine only in the presence of 11.1% HCHO. The baseline-corrected voltammograms (FIG. 1b) reveal an additional peak (12) at 1.25 V, which corresponds to the oxidation potential of the characteristic peak of methamphetamine (i.e. mono-methylated amphetamine), suggesting that the peak (11) at 1.03 V is due to di-methylated amphetamine. This is further discussed below.

Principle Involved and Confirmation Through Mass Spectrometry

Figure 2:
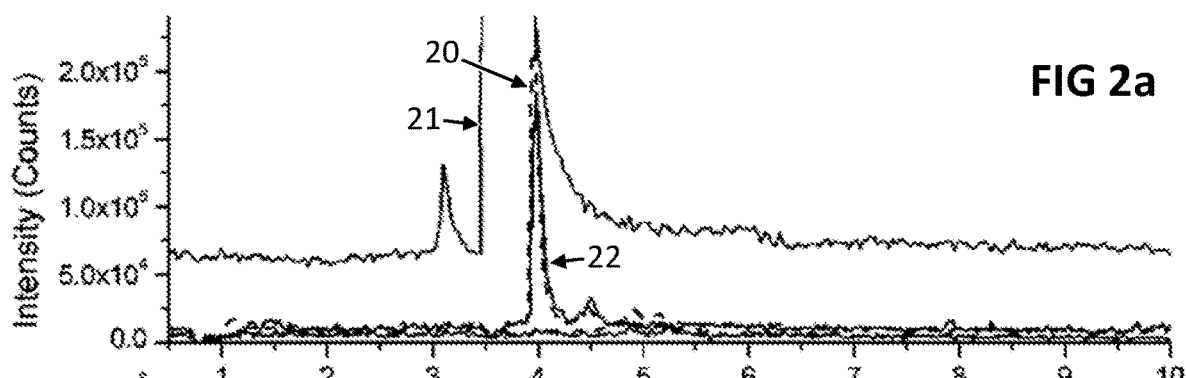
FIG. 2, including
Figure 2:
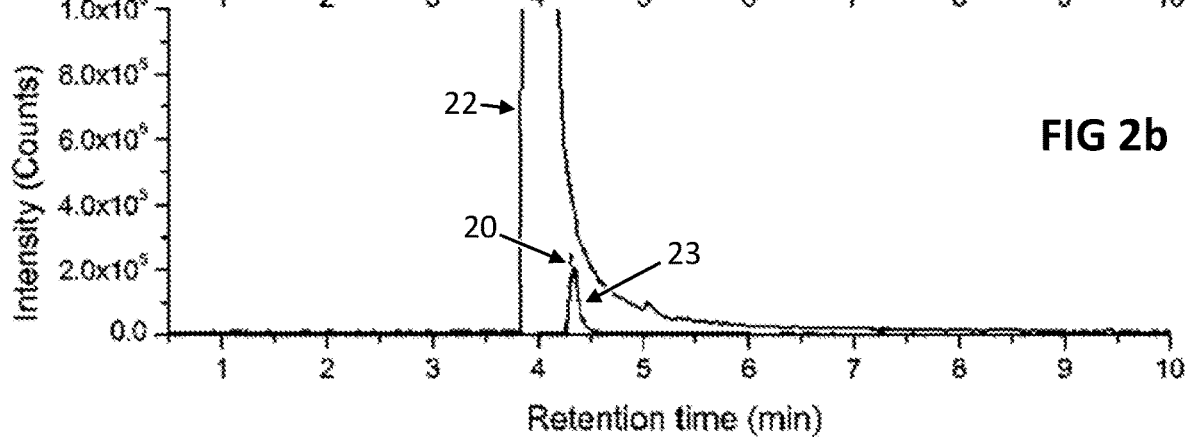
Figure 2:
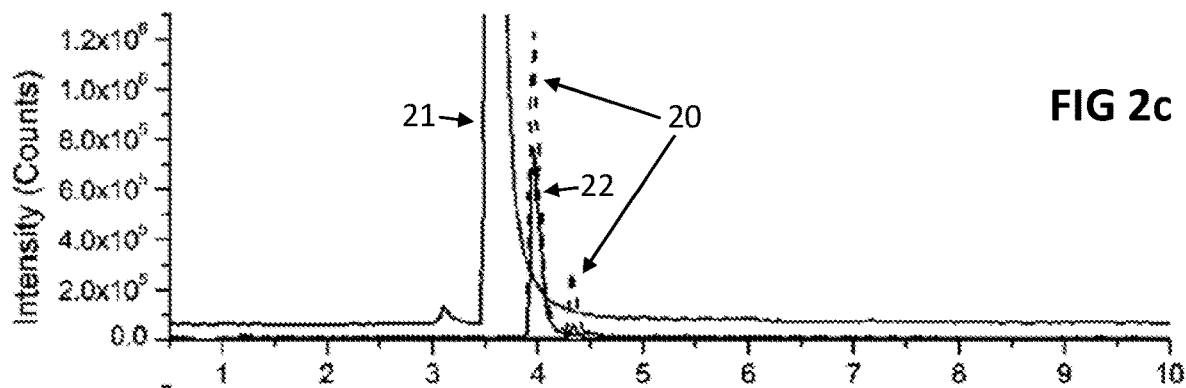
Figure 2:
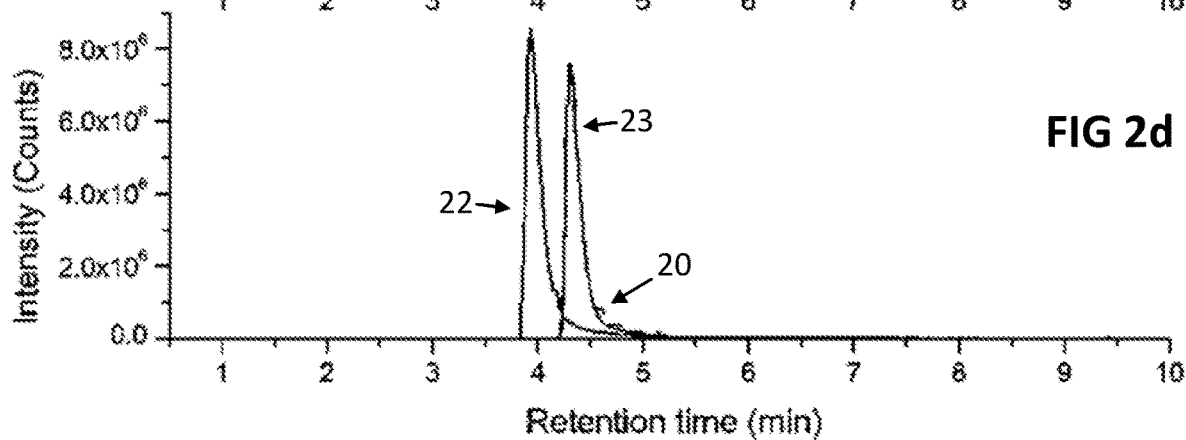

Formaldehyde reactions with amphetamine and methamphetamine were studied using LC-QTOFMS analysis to confirm which electroactive products are formed during the reaction with formaldehyde. Here, 1 mM solutions of amphetamine and methamphetamine were prepared in 0.1 M KCl and 0.02 M $KH_2PO_4$ phosphate (PBS) buffer solution containing 11.1% formaldehyde in both pH 7 and 12 and were left to react for one hour. Afterwards, the samples were diluted to 20 ng/µL with ultrapure water and directly injected. The obtained chromatograms (dashed lines 20) are compared in FIG. 2 (a and c, respectively) to a 20 ng/µL standard of amphetamine (solid lines 21) and methamphetamine (solid lines 22).

One main reaction product was formed during the formaldehyde treatment in both conditions (pH 7 and pH 12). The product elutes at 3.94 min (m/z 150.1226, $C_{10}H_{15}N$), just after the remaining amphetamine at 3.59 min (m/z 136.1121, $C_9H_{13}N$). After comparing the elution time, mother-ion and fragmentation pattern of this and methamphetamine (m/z 150.1226, $C_{10}H_{15}N$), we can positively deduce that by this treatment the redox inactive amphetamine is partially converted into methamphetamine. Moreover, a secondary product at 4.47 min was found in pH 12 conditions which correspond to the di-methylated form of amphetamine (m/z 164.1434, $C_{11}H_{17}N$). As a control experiment a sample of methamphetamine as starting material, instead of amphetamine, was subjected to the same reaction conditions and LC-QTOF analysis, and compared to methamphetamine (solid lines 22) and dimethamphetamine (solid lines 23) (FIGS. 2b and d). Here, the elution time, mother-ion and fragmentation pattern pointed towards the di-methylated form of amphetamine. No additional products were observed.

Based on these findings, we tentatively suggest that under these conditions a kind of in-situ Eschweiler-Clarke methylation reaction is created (cf. supra).

Optimization of Parameters

Initially, reaction and measurement parameters were optimized to find out the best experimental conditions for the amphetamine detection strategies. More specifically, the amount of formaldehyde in the measurement environment to give the maximal signal for the analyte, the reaction time required before measurement and the influence of adding formate to the buffer solutions were studied.

The concentration of formaldehyde in the measuring environment influences the reaction rate and amount of analyte converted into the electrochemically detectable product. Optimization of this parameter is therefore useful. Since the pKa values of amphetamine and formaldehyde are 9.9 and 13.27 (at 25° C.) respectively, this optimization was carried out at a neutral pH (pH 7) and at an alkaline pH (pH 12) to gain an insight in how the detection of protonated and deprotonated forms of amphetamine with formaldehyde might different. Baseline corrected square-wave voltammograms (not depicted) were recorded of 1 mM amphetamine at different concentrations of formaldehyde in PBS buffer solution at pH 7 (concentrations of 3.7%, 5.6%, 7.4%, 9.25%, 11.1% and 13% HCHO were measured) and pH 12 (concentrations of 3.7%, 5.6%, 7.4% and 9.25%, HCHO were measured). Measuring buffer containing 11.1% formaldehyde gave maximum current values at pH 7 while at pH 12, maximum current was obtained at 3.7% HCHO concentration. The decrease after these threshold limits appears to be due to the increasingly high backgrounds, which overlay the actual oxidation signal and therefore complicate its detection. Optimization of the reaction time was also carried out to check how fast the measurements can be performed once amphetamine is mixed with the buffer solution containing formaldehyde (time-to-result) by recording baseline-corrected square-wave voltammograms (not depicted) of 1 mM amphetamine at different time intervals ranging from 0 to 60 min in PBS buffer solution at pH 7 and 12. It was found that the reaction takes place quickly and measurements within a minute or at one minute showed a high signal in both pH 7 and pH 12, while a longer reaction time did not drastically increase the current.

Figure 3:
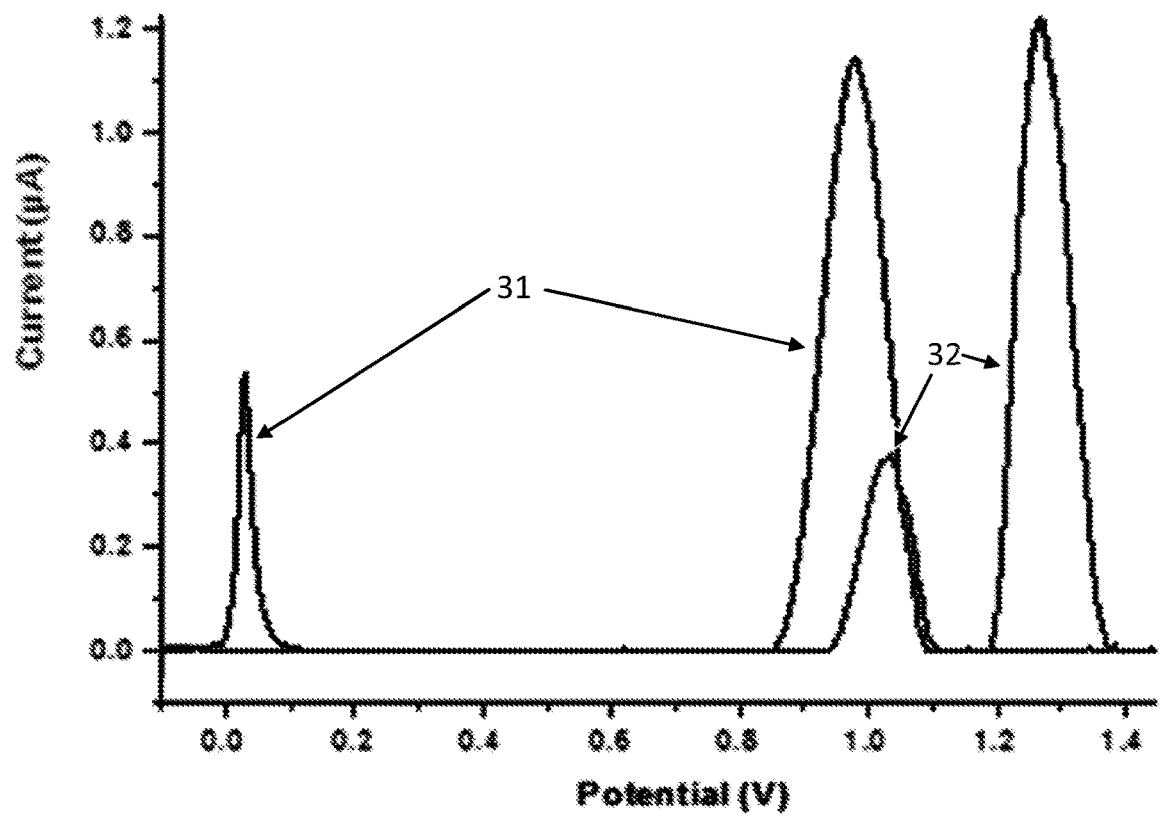
FIG. 3 shows square-wave voltammograms of 1 mM amphetamine in the presence (31) and absence (32) of sodium formate (20 vol %) at pH 7 in a 10 vol % formaldehyde, 0.1 M potassium chloride and 0.1 M potassium phosphate buffer solution.

In view of the Eschweiler-Clarke reaction scheme, it was believed that sodium formate, acting as a reducing agent (e.g. a source of hydride), might facilitate the methylation reactions. Since could be preferred to limit the concentration of formaldehyde as much as possible due to its potential toxicity, it was tested if sodium formate could be added to maintain enough methylation for electrochemical measurements. Buffers with higher salt concentrations were chosen in order to provide higher buffering capacity to compensate for the addition of formate. The buffer contained 10 vol % of 37% formaldehyde, 20 vol % of 10 M sodium formate, 0.1 M potassium chloride and 0.1 M potassium phosphate, and is hereafter referred to as formaldehyde-formate buffer solution (FFBS). The concentrations of formate and formaldehyde here were fixed after optimization to get maximum peak current. Square-wave voltammograms (FIG. 3) of amphetamine indeed showed a higher signal for the peak at ca. 1.0 V when formate was added to the measuring solution (31), compared to the one without formate (32). At pH 12 however (not depicted), adding formate led to fluctuations in the measurements and high backgrounds, complicating detection. Thus, when using FFBS, measuring at pH 7 offered the best results.

Electrochemical Detection of Amphetamine in Street Samples

Figure 4:
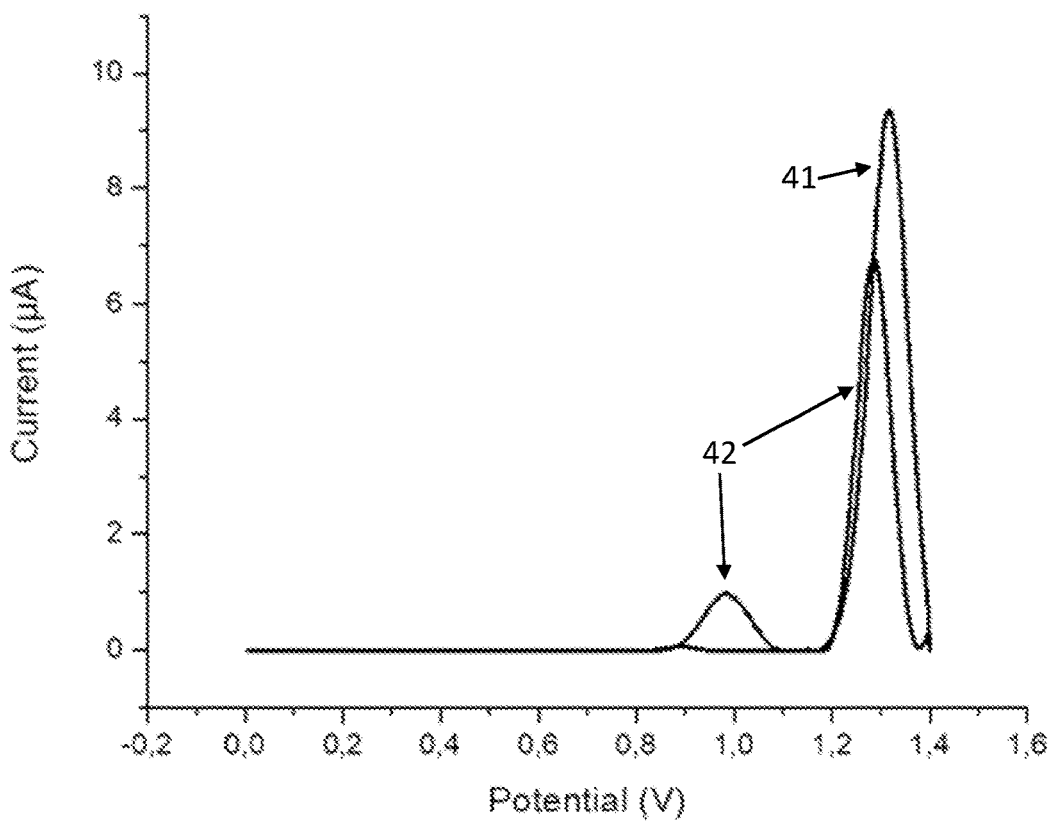
FIG. 4 shows square-wave voltammograms of 1 mg/mL street sample in phosphate buffer solution (41) and formaldehyde-formate buffer solution (42) at pH 7.

A street sample containing amphetamine was obtained from NICC (National Institute for Criminalistics and Criminology, Brussels) and was electrochemically analysed. According to the confirmatory report from NICC, the sample contained amphetamine and caffeine as active ingredients. Approximately 1 mg the sample (e.g. 1 µL of 100 mM of sample stock) was taken and vortexed briefly (e.g. 5 s) in vials containing 1 ml of the measuring buffer solutions. FIG. 4 shows square-wave voltammograms of a 1 mM sample containing amphetamine measured in PBS (41) and FFBS (42). The voltammogram from using PBS (41) only contains an oxidation peak at 1.32 V, which corresponds to the oxidation potential of caffeine. When the FFBS (42) is used, it clearly depicts the characteristic peak at 1.0 V indicating the additional presence of amphetamine. This indicates the technique's ability to detect the primary amine even when mixed with other compound and even in the presence of a crude sample matrix which might contain starch or any other tabletting powders.

Example 1b: Modifying the Sensing Surface with Paraformaldehyde (Strategy 2)

Embedded in a Matrix

Knowing that formaldehyde makes primary amines electrochemically detectable, other strategies were tested to apply the same principle, but through a different approach. One of those was the modification of the working electrode surface with paraformaldehyde (PFA), as a source of formaldehyde, embedded in a hydrogel matrix. This polymer is more stable than a formaldehyde solution (which e.g. contains stabilizers like methanol to prevent polymerization and/or oxidation). Without being bound by theory, it is believed that when such a modified working electrode surface encounters an alkaline buffer, the hydrogel swells and PFA diffuses out into the measuring buffer solution with alkaline pH. The alkaline pH (e.g. pH 12) also depolymerizes PFA into formaldehyde which in turn causes the methylation. Since the pH is beyond the pKa of (most) primary amines, better current peak signals with low background were obtained when formate and high concentrations of salts (e.g. FFBS buffer) were not used. Hence this strategy involved a measuring buffer containing 0.02 M potassium phosphate and 0.1 M potassium chloride (PBS) buffer with pH 12.

The working electrode surface modification was performed by first heating a mixture of 1.5 wt % gelatine Gel B in pH 7 PBS in an Eppendorf tube to 40° C. for 15 min followed by additional mixing until the solution became homogeneous. 20 mg/mL PFA was then gently mixed into the 1.5% gelatine, after which a 5 µl of this mix was dropped onto the working electrode and allowed to air dry for 45 min. A 1 mM sample solution was prepared as in example 1a and 80 µL of the sample solution was dropped on the electrode. Measurements were then standardly performed after 1 min waiting time since sample introduction.

Figure 8:
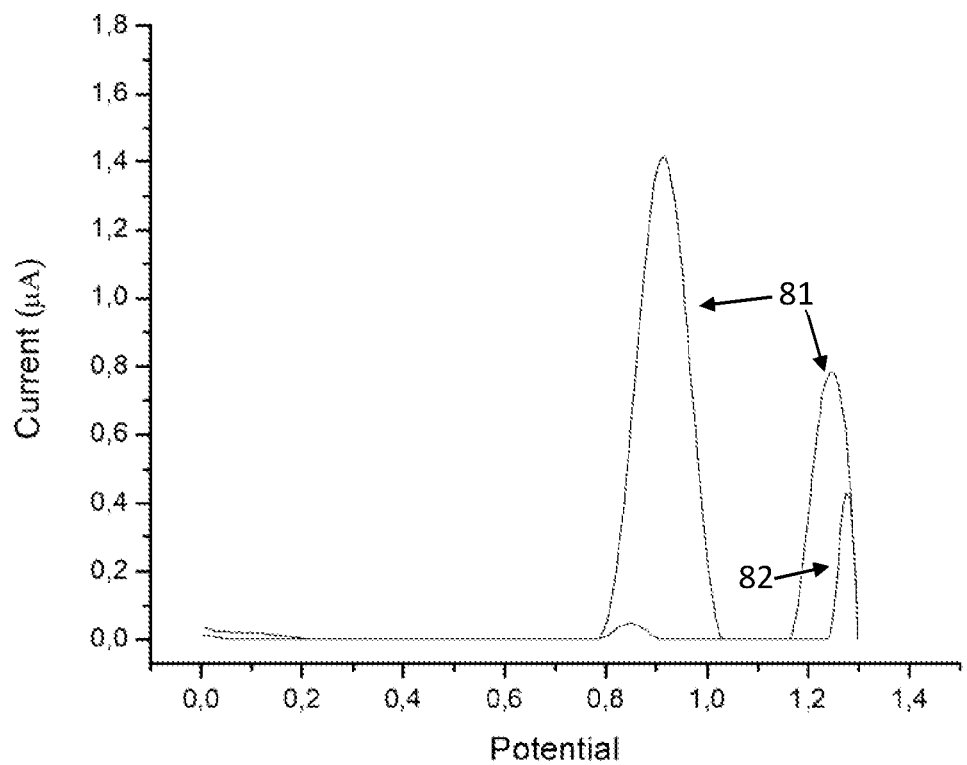
FIG. 8 shows square-wave voltammograms of 1 mM amphetamine (81) and of a blank sample (82) in pH 12 phosphate buffer using a carbon screen-printed electrode modified at the working electrode with 5 μL of 20 mg/mL paraformaldehyde in a 1.5% gelatine matrix. Measurements were carried out after a wait time of 1 minute.
Figure 9:
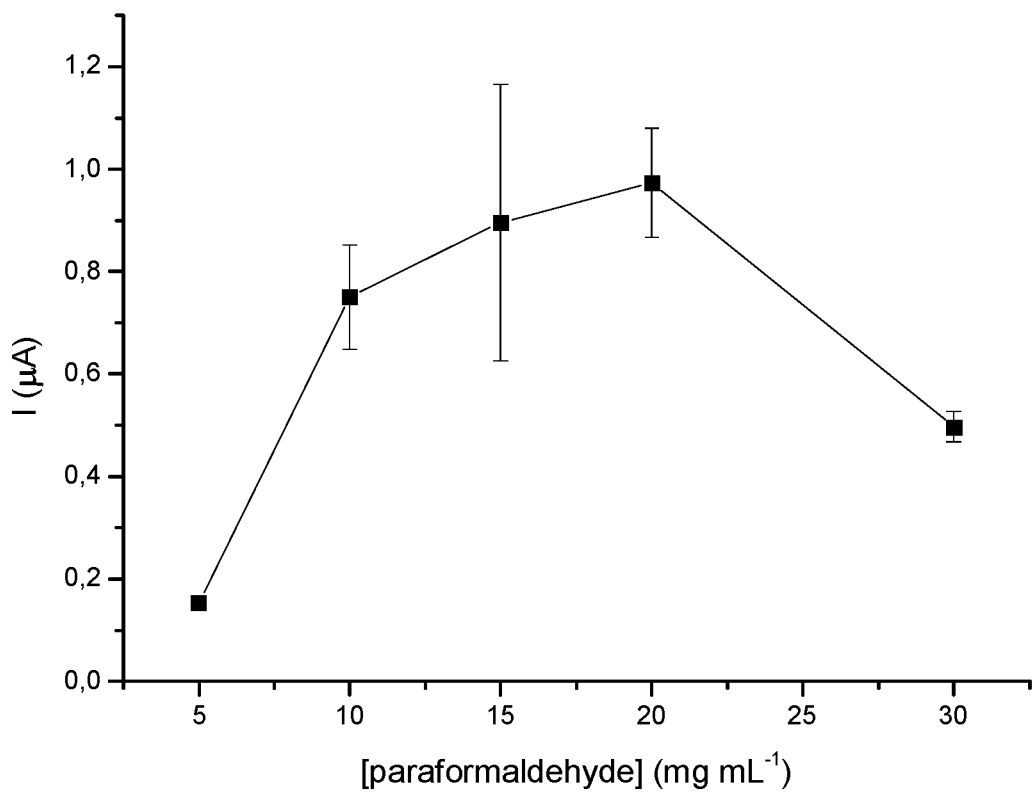
FIG. 9 shows a curve of the measured current for 1 mM amphetamine in function of the concentration of paraformaldehyde used in a 1.5% gelatine matrix.
Figure 10:
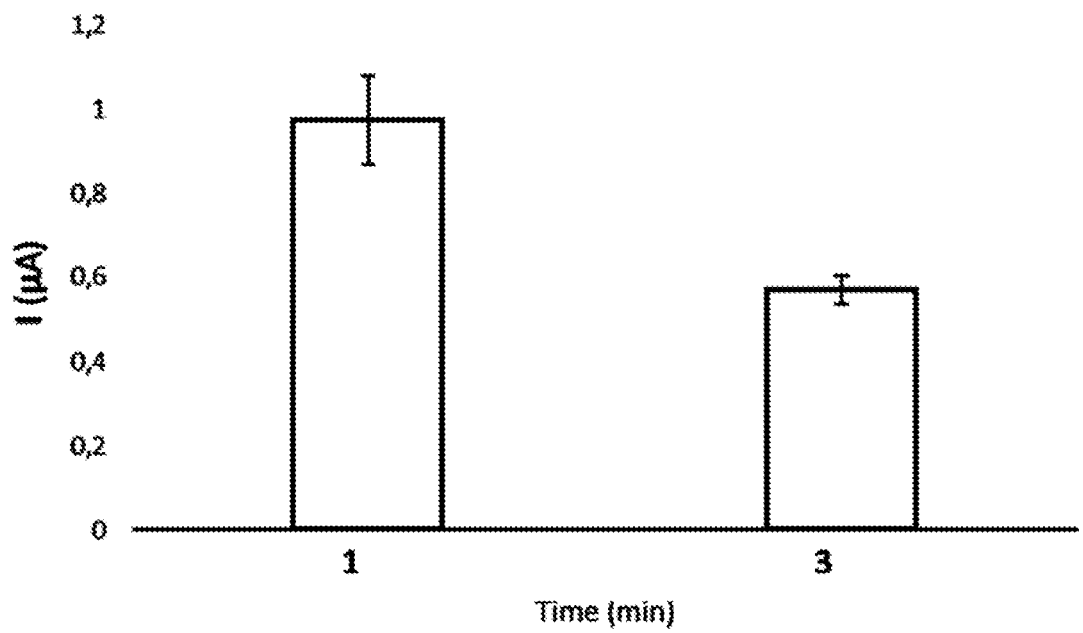
FIG. 10 shows a bar chart of the measured current for 1 mM amphetamine using a carbon screen-printed electrode modified at the working electrode surface with 20 mg/mL PFA in 1.5% gelatine in function of the wait time before measuring.

FIG. 8 shows the voltammograms of 1 mM amphetamine (81) and of a blank sample (82) at the PFA-gelatine modified electrodes. The influence of the amount of PFA in the gelatine matrix was studied (FIG. 9) and 20 mg/mL was selected as an optimal concentration yielding maximum current values. The waiting time between introducing the sample solution and starting the measurement was optimized (FIG. 10) in function of having (i) the gelatine swell and (ii) PFA diffuse into the measuring solution. It was found that measurements at ca. 1 min gave maximum signals, giving the diffusion of PFA into the system an optimal amount of time. After this time period, the peak currents reduced due to saturation from high background current.

Without Matrix

A working protocol for forming a coating of paraformaldehyde as such—i.e. without a separate matrix—was also developed. In this approach, PFA was dispersed in 70% ethanol to yield a 20 mg/mL PFA suspension. This suspension was drop cast directly onto a screen-printed electrode and left to dry for 1 hour.

Figure 13:
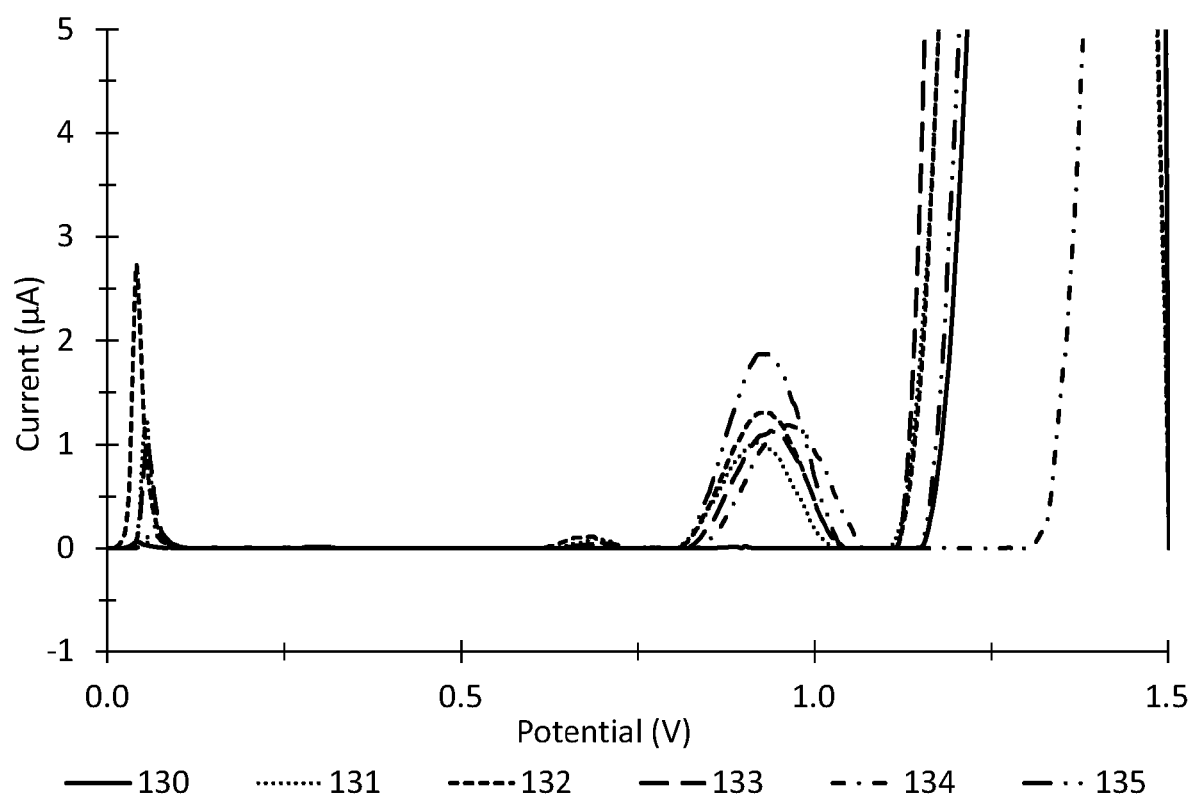
FIG. 13 shows square-wave voltammograms of 5 measurements (131-135) of 1 mM amphetamine and of a blank sample (130) in pH 12 PBS buffer using screen-printed electrodes modified with a paraformaldehyde coating (130).

Analogous to the previous experiments, a 1 mM amphetamine sample solution was then prepared in pH 12 PBS buffer containing 0.1 M potassium phosphate and 0.1 M potassium chloride. About 85 µL of this sample solution was dropped on the electrode and measured after 1 min. FIG. 13 shows the voltammograms of 5 such measurements (131-135) and of a blank sample (130). A summary of the results is also shown in the following table:

| Measurement | Oxidation potential (V) | Peak current (µA) |
|---|---|---|
| 1 | 0.92 | 1.0 |
| 2 | 0.93 | 1.3 |
| 3 | 0.94 | 1.1 |
| 4 | 0.95 | 1.2 |
| 5 | 0.92 | 1.9 |
| mean | 0.93 | 1.3 |
| standard deviation | 0.01 | 0.3 |

Example 1c: Mixing Paraformaldehyde in Alkaline Measuring Solution (Strategy 3)

Figure 11:
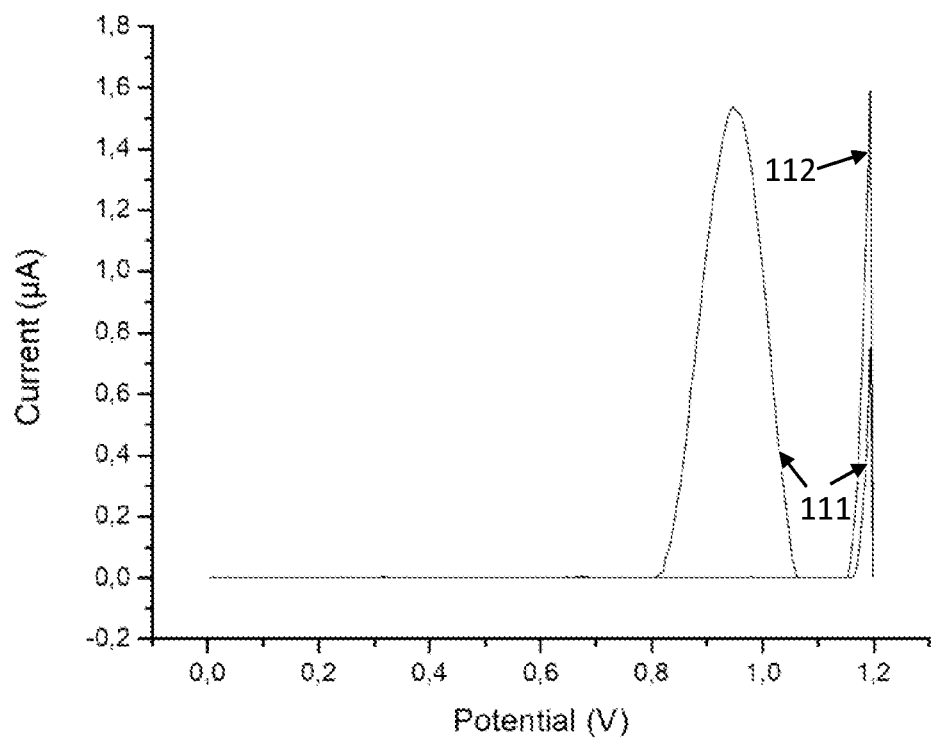
FIG. 11 shows square-wave voltammograms of 1 mM amphetamine (111) and of a blank sample (112) in pH 12 phosphate buffer comprising 20 mg/mL paraformaldehyde.

Paraformaldehyde could also be introduced in the system without any coating on the surface of the electrode. This was done by simply mixing PFA into a pH 12 buffer solution prior to the measurement. The first step in this strategy involved the mixing of sample (e.g. 5 mg) in pH 12 phosphate buffer (e.g. 1 mL) containing 0.1 M potassium chloride and 0.1 M potassium phosphate. Here, the higher potassium phosphate concentration was selected so as to not shift the pH too much upon mixing PFA in the buffer. Afterwards, this solution was mixed with PFA in powder form (to a PFA concentration of 20 mg/mL) and 80 µL was pipetted on the screen-printed electrodes. Measurements were carried out immediately after introduction of the measuring buffer containing the sample onto the screen-printed electrodes. FIG. 11 shows that applying this strategy resulted in a clear peak at 0.95 V for amphetamine.

Example 2: Electrochemical Analysis of Other Classes of Primary Amines

Other drug classes, antibiotics and amino acids were tested for their electrochemical behaviour in the presence of FFB solution. Samples with a target concentration of 1 mM were prepared and electrochemically analysed in both PBS and FFBS as previously explained in example 1a. FIG. 5 shows the square-wave voltammograms of different classes of analytes containing primary amines, namely fluoroamphetamine (a), 2-aminoindane (b), dimethocaine (c), cephalexin (d), amoxycycline (e), phenyl glycine (f), glycine (g) and histidine (h). The voltammograms using FFBS (right side of FIG. 5) clearly show peaks (marked by an arrow) that indicate the presence of the analyte, while in some cases the fingerprint is enriched by the emergence of new peaks.

Figure 12:
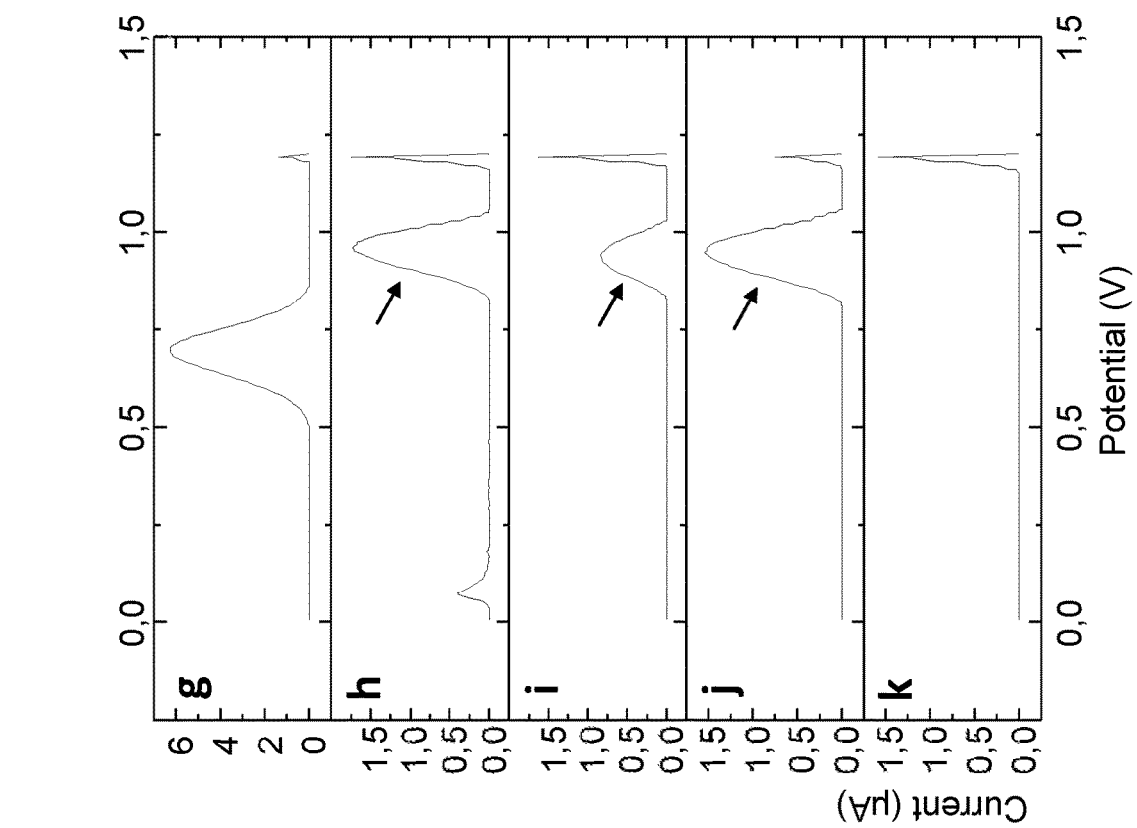
FIG. 12 shows square-wave voltammograms of 1 mM ampicillin (a), amoxicillin (b), dimethocaine (c), mephedrone (d), butylone (e), methylenedioxymethamphetamine (MDMA) (f), methamphetamine (g), aminoindane (h), 3-fluoroamphetamine (i), amphetamine (j) and a blank (k) in pH 12 phosphate buffer comprising 20 mg/mL paraformaldehyde.
Figure 12:
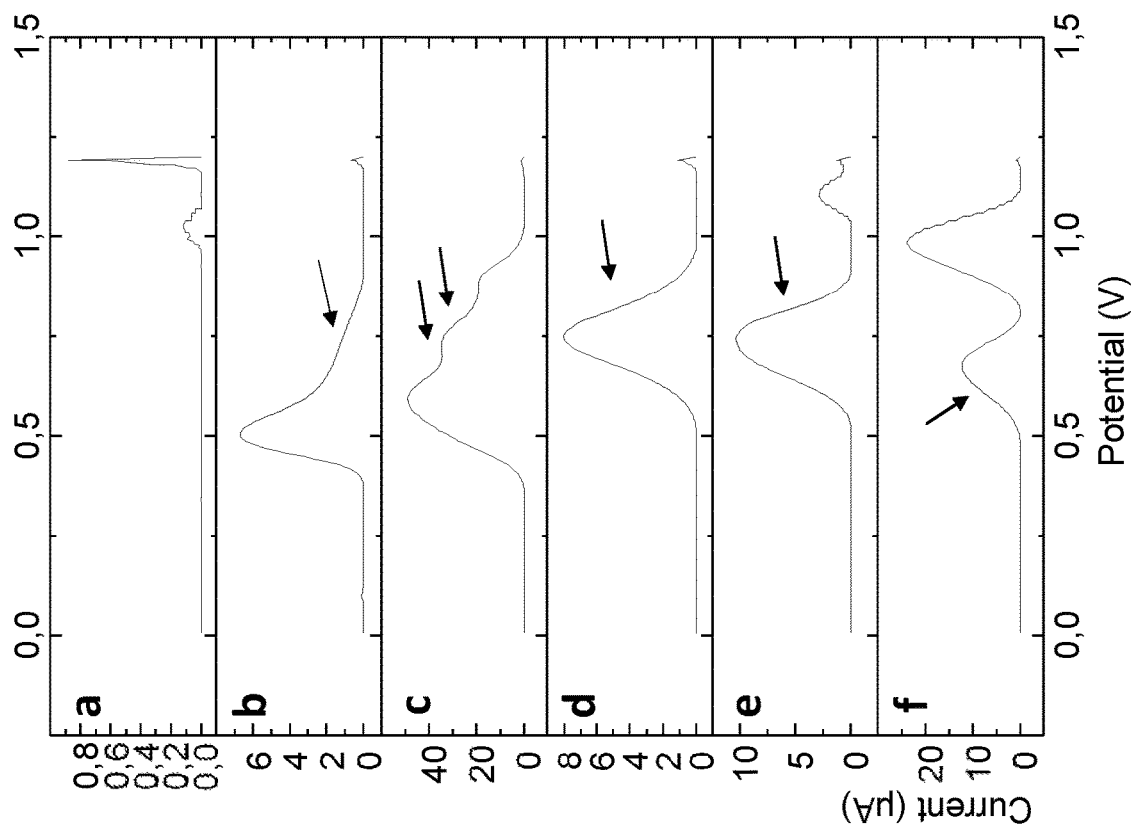

Other drugs classes can likewise be measured using strategy 2 (example 1b) or 3 (example 1c). FIG. 12 show the result of 1 mM of samples of 1 mM ampicillin (a), amoxicillin (b), dimethocaine (c), mephedrone (d), butylone (e), methylenedioxymethamphetamine (MDMA) (f), methamphetamine (g), aminoindane (h), 3-fluoroamphetamine (i), amphetamine (j) and a blank (k) measured through strategy 3, wherein the emerging peaks are indicated by an arrow.

Example 3: Enriching the Electrochemical Fingerprint of Secondary Amines

Secondary amines are electrochemically active and can be detected in most of the common measuring conditions. However, when secondary amines are further methylated using FFBS, a combination of methylated and non-methylated product is typically present, resulting in a combined fingerprint of these two forms, thus enriching the resulting electrochemical fingerprint. This is useful to discriminate between compounds in samples containing complex mixtures of compounds. For example, street samples of drugs of abuse usually occur as mixtures between the drug and a variety of adulterants, precursors and cutting agents. Likewise, amines in environmental analysis such as antibiotics in wastewater or other effluents, can often found be together with interferents (which could be compounds of interest themselves). When electrochemically analysed, signals from different compounds can overlap or can give a broad signal, making it difficult to conclude the composition of the sample. By screening them with and without formaldehyde in the measuring conditions, a unique fingerprint can be obtained for each of these compounds.

Figure 6A:
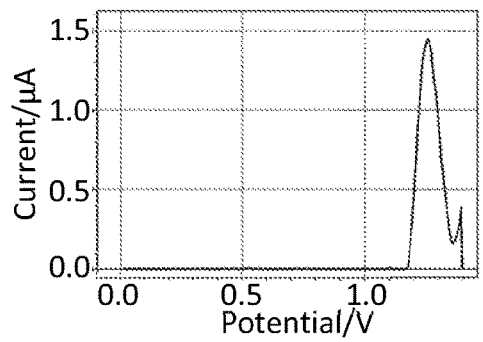
FIGS. 6a to 6e, shows square-wave voltammograms of 1 mM secondary amine methamphetamine (6a), 3,4-methylenedioxymethamphetamine (MDMA) (6b), butylone (6c), mephedrone (6d) and dimethocaine (6e) in pH 7 phosphate buffer solution (left) and pH7 formate-formaldehyde buffer (right).
Figure 6B:
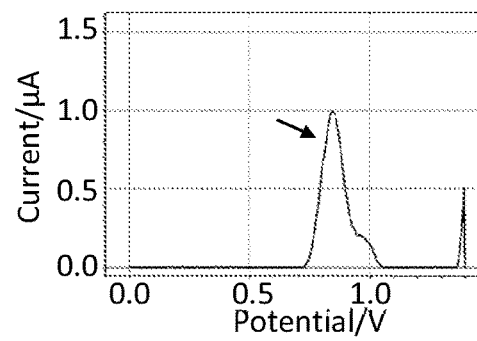
Figure 6B:
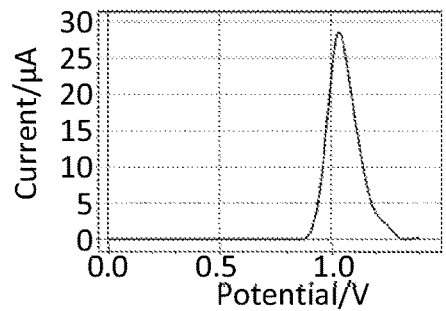
Figure 6C:
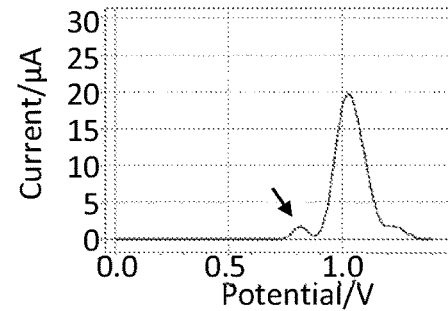
Figure 6C:
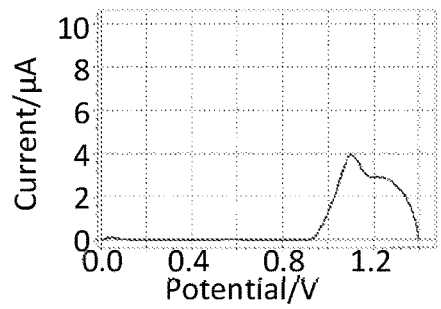
Figure 6D:
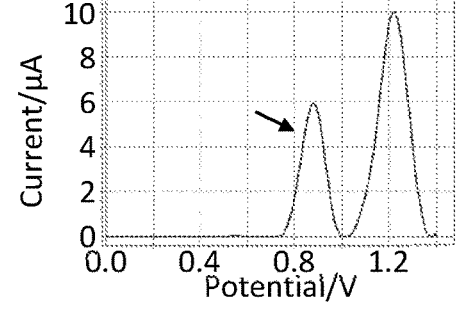
Figure 6D:
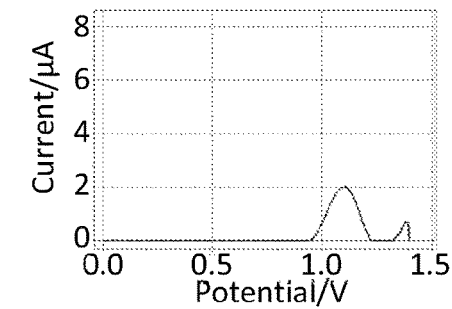
Figure 6E:
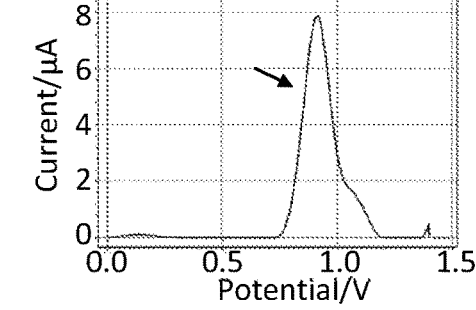
Figure 6E:
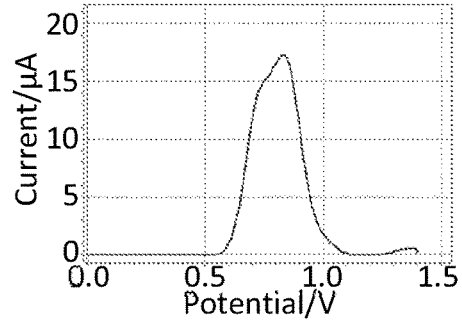
Figure 6:
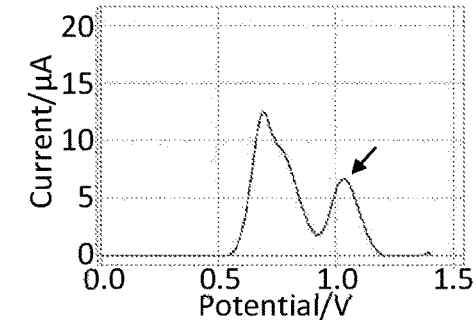
FIG. 6, including

An example is methamphetamine, another stimulant drug in the ATS category. Electrochemical analysis of methamphetamine in PBS without any formaldehyde (left side of FIG. 6*a*) showed a peak at a higher potential (1.3 V) at pH 7 attributed to oxidation of the secondary amine. However, when pH 7 FFBS was used (right side of FIG. 6*a*), methamphetamine was methylated and a peak was observed at 0.8 V with a shoulder-like feature at 0.95 V. This illustrates how using a dual approach with and without formaldehyde can enrich the fingerprint of secondary amine-containing compounds. FIGS. 6*b-e* depict the voltammograms of some further common secondary amines from the drugs class in the absence (left side) and presence (right side) of formaldehyde, namely 3,4-methylenedioxymethamphetamine (MDMA) (b), butylone (c), mephedrone (d) and dimethocaine (e).

Example 4: Other Electrochemical Techniques

Linear sweep voltammetry (LSV) and chronoamperometry were performed to investigate the validity of the present invention with respect to other electrochemical techniques. FIG. 7 shows the linear sweep voltammograms (7*a*) and chronoamperograms (7*b*) for 1 mM solution of amphetamine detected with PBS (71) and FFBS (72). The voltammogram of 1 mM amphetamine in FFBS showed a small oxidation peak at ca. 1.0 V which is absent in the voltammogram of 1 mM amphetamine in PBS indicating the applicability of the strategy to other voltammetry techniques. Amperometry at this peak potential shows increased currents for every 1 mM amphetamine added (indicated by downward pointing arrows) to the FFBS and none when added to PBS, indicating that this strategy can also be used in electrochemical measurements with a constant potential.

It is to be understood that although preferred embodiments, specific constructions and configurations, as well as materials, have been discussed herein for devices according to the present invention, various changes or modifications in form and detail may be made without departing from the scope and technical teachings of this invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for electrochemically detecting a primary or secondary amine, comprising:
   (a) providing a sample which potentially comprises the primary or secondary amine;
   (b) contacting the sample with a source of formaldehyde, thereby, if present, methylating the primary or secondary amine to yield a methylated amine;
   (c) performing an electrochemical technique on the sample to obtain measurement results concerning the methylated amine, and
   (d) analysing the measurement results;
   wherein the source of formaldehyde is an adduct of formaldehyde; and
   wherein step b comprises:
   (b1) bringing the sample in contact with an electrochemical electrode comprising a coating of the source of formaldehyde.

2. The method according to claim 1, wherein the sample is an aqueous solution.

3. The method according to claim 1, wherein step b is performed under conditions of neutral or basic pH.

4. The method according to claim 3, wherein step b is performed under conditions of basic pH.

5. The method according to claim 1, wherein a duration between the start of step b and the start of step c is from 0 s to 60 min, preferably from 15 s to 20 min.

6. The method according to claim 1, wherein the electrochemical technique comprises a voltammetry or amperometry.

7. An electrochemical electrode for use in a method according to claim 1, comprising a coating of a source of formaldehyde;
   wherein the source of formaldehyde is an adduct of formaldehyde.

8. The electrochemical electrode according to claim 7, wherein the coating comprises a matrix and the source of formaldehyde.

9. The electrochemical electrode according to claim 8, wherein the matrix is gelatine.

10. The electrochemical electrode according to claim 7, comprising a working electrode, a counter electrode and a reference electrode, and
    wherein the coating of the source of formaldehyde covers the working electrode.

11. The method according to claim 1, wherein the adduct of formaldehyde is a homooligomer, a homopolymer, a heterooligomer or a heteropolymer.

12. The method according to claim 1, wherein the adduct of formaldehyde is paraformaldehyde or 1,3,5-trioxane.

13. A method for electrochemically detecting a primary or secondary amine, comprising:
   (a) providing a sample which potentially comprises the primary or secondary amine;
   (b) contacting the sample with a source of formaldehyde, thereby, if present, methylating the primary or secondary amine to yield a methylated amine;
   (c) performing an electrochemical technique on the sample to obtain measurement results concerning the methylated amine, and
   (d) analysing the measurement results;
   wherein the source of formaldehyde is an adduct of formaldehyde; and
   wherein step b comprises:
   (b1) bringing the sample in contact with an electrochemical electrode comprising a coating of the source of formaldehyde, or
   (b2) forming a mixture of the sample and the source of formaldehyde;
   wherein the adduct of formaldehyde is a homooligomer, a homopolymer, a heterooligomer or a heteropolymer.

* * * * *